(12) United States Patent
Donofrio

(10) Patent No.: US 7,261,106 B2
(45) Date of Patent: Aug. 28, 2007

(54) RESPONSE TESTING FOR CONSCIOUS SEDATION UTILIZING A CANNULA FOR SUPPORT/RESPONSE

(75) Inventor: William T. Donofrio, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 550 days.

(21) Appl. No.: 10/670,453

(22) Filed: Sep. 25, 2003

(65) Prior Publication Data

US 2005/0066971 A1   Mar. 31, 2005

(51) Int. Cl.
*A61M 16/00* (2006.01)
(52) U.S. Cl. .................. 128/204.21; 600/301; 604/65; 604/66
(58) Field of Classification Search ........... 128/203.12, 128/204.21, 204.23, DIG. 12, DIG. 13; 600/300, 600/544; 604/64, 65, 66
See application file for complete search history.

(56) References Cited

U.S. PATENT DOCUMENTS

| 5,614,887 | A |   | 3/1997 | Buchbinder |   |
|---|---|---|---|---|---|
| 6,024,088 | A | * | 2/2000 | Ishikawa et al. | 128/204.21 |
| 6,807,965 | B1 | * | 10/2004 | Hickle | 128/204.23 |
| 2002/0017296 | A1 |   | 2/2002 | Hickle |   |
| 2002/0017299 | A1 |   | 2/2002 | Hickle |   |
| 2002/0017300 | A1 |   | 2/2002 | Hickle et al. |   |
| 2002/0188259 | A1 |   | 12/2002 | Hickle |   |
| 2003/0189492 | A1 | * | 10/2003 | Harvie | 340/573.1 |

* cited by examiner

*Primary Examiner*—Steven O. Douglas
(74) *Attorney, Agent, or Firm*—Verne E. Kreger

(57) ABSTRACT

A conscious sedation system and a cannula and response testing assemblage for a conscious sedation system. In one embodiment, a controller generates a request for a predetermined response from a patient and analyses at least a response made by the patient to the request to determine a level of sedation of the patient. A cannula is disposable on the face of the patient for monitoring the breathing of the patient. A request assembly communicates to the patient the request generated by the controller. A response assembly senses the response and communicates the response to the controller. At least a part of at least one of the request and response assemblies is supported by the cannula. In another embodiment, the cannula itself is used as the response assembly wherein the response is a breathing response of the patient to the request.

22 Claims, 31 Drawing Sheets

US 7,261,106 B2

1

RESPONSE TESTING FOR CONSCIOUS SEDATION UTILIZING A CANNULA FOR SUPPORT/RESPONSE

FIELD OF THE INVENTION

The present invention relates generally to conscious sedation systems, and more particularly to a conscious sedation system having a response testing apparatus and a cannula and to a cannula and response testing assemblage for a conscious sedation system.

BACKGROUND OF THE INVENTION

Known conscious sedation systems include a conscious sedation system disclosed in United States Patent Application Publication No. 2002/0017299. In that system, a controller generated a request for a predetermined response from a patient. The request was in the form of an auditory command which was received by a patient through an earphone in the ear of the patient or was in the form of a vibration signal which was received by the patient through a vibrator in a handpiece which was attached to the hand of the patient. The predetermined response to the request was the pushing of a button on the handpiece by the patient which closed a switch sending a signal to the controller. The controller analyzed medical information from the patient (such as blood pressure and other information) and analyzed the time delay between the request and the response to determine a level of sedation of the patient. When the time delay between the request and the response increased, the controller determined that the patient was in a deeper level of sedation and decreased the flow of a conscious sedation drug to the patient. It is known to have a number of volume settings for the auditory command and to initially manually raise the volume setting before the start of conscious sedation until a fully conscious patient says he or she can hear the auditory command. It is also known that doctors using a similar system have themselves asked the patient by name to squeeze the handpiece.

What is needed is an improved conscious sedation system and/or component thereof and/or method therefor. This invention addresses those needs lacking in known conscious sedation systems and/or components thereof and/or methods therefor.

SUMMARY OF THE INVENTION

A first expression of a first embodiment of the invention is for a conscious sedation system including a controller, a cannula, and a response testing apparatus. The controller generates a request for a predetermined response from a patient and analyses at least a response made by the patient to the request to determine a level of sedation of the patient. The cannula is disposable on the face of the patient proximate at least one of the nose and the mouth of the patient for monitoring the breathing of the patient. The response testing apparatus includes a request assembly and a response assembly. The request assembly communicates to the patient the request generated by the controller. The response assembly senses the response and communicates the response to the controller. At least a part of at least one of the request and response assemblies is supported by the cannula.

An alternate expression of the first embodiment of the invention is for a cannula and response testing assemblage for a conscious sedation system and includes a cannula and a response testing apparatus. The cannula is disposable on the face of a patient proximate at least one of the nose and the mouth of the patient for monitoring the breathing of the patient. The response testing apparatus includes a request assembly and a response assembly. The request assembly communicates to the patient a request generated by a controller of the conscious sedation system for a predetermined response from the patient. The response assembly senses a response made by the patient to the request and communicates the response to the controller which analyses at least the response to determine a level of sedation of the patient. At least a part of at least one of the request and response assemblies is supported by the cannula.

Another embodiment of the invention is for a conscious sedation system including a controller and a response testing apparatus. The controller generates a request for a predetermined breathing response from a patient and analyses at least a breathing response made by the patient to the request to determine a level of sedation of the patient. The response testing apparatus includes a request assembly and a cannula. The request assembly communicates to the patient the request generated by the controller. The cannula is disposable on the face of the patient proximate at least one of the nose and the mouth of the patient for monitoring the breathing of the patient, wherein the cannula is operatively connected to the controller.

The present invention has, without limitation, application in conscious sedation systems used during the performance of medical procedures such as colonoscopies, robotic-assisted surgery, etc.

BRIEF DESCRIPTION OF THE DRAWINGS

FIG. 1-2 is a side-elevational view of an example of a part of the request assembly of FIG. 1-1 in the form of an auditory request assembly;

FIG. 1-3 is a front-elevational view of an example of a part of the request assembly of FIG. 1-1 in the form of a vibratory request assembly;

FIG. 1-4 is a front-elevational view of an example of a part of the response assembly of FIG. 1-1 in the form of a switch response assembly;

FIG. 2-1 is a schematic diagram of a first embodiment of a second aspect of the present invention showing a conscious sedation system including a controller, a cannula, and a response testing apparatus which includes a request assembly supported by the cannula and which includes a response assembly;

FIG. 2-2 is a perspective view of an example of the cannula of FIG. 2-1 without the supported request assembly;

FIG. 2-3 is a schematic diagram of a second embodiment of a second aspect of the present invention showing a conscious sedation system including a controller, a cannula, and a response testing apparatus which includes a request assembly and which includes a response assembly supported by the cannula;

FIG. 2-4 is an enlarged schematic diagram of the response assembly and a portion of the cannula of FIG. 2-3;

FIG. 2-5 is a schematic diagram of a third embodiment of a second aspect of the present invention showing a conscious sedation system including a controller and including a response testing apparatus which includes a request assembly and which includes a cannula which is also used as a response assembly;

FIG. 3-1 is a graph of a vibration set comprising vibratory pulses utilizing predetermined time intervals between pulses in applying the vibration stimuli;

FIG. 3-2 is a graph of a vibration set comprising vibratory pulses utilizing predetermined duration of pulses in applying the vibration stimuli;

FIG. 3-3 is a schematic diagram of an embodiment of a third aspect of the present invention showing a conscious sedation system including a controller and including a response testing apparatus which includes a request assembly and a response assembly;

FIG. 3-4 is a block diagram of an embodiment of the method of the present invention using the conscious sedation system;

FIG. 4-1 is a schematic diagram of a first embodiment of a fourth aspect of the present invention showing a conscious sedation system including a controller and including a response testing apparatus which includes a request assembly and a response assembly;

FIG. 4-2 is a front-elevational view of an example of the response assembly of FIG. 4-1 in the form of a handpiece;

FIG. 4-3 is a schematic diagram of the handpiece of FIG. 4-2 including three mutually orthogonal accelerometers;

FIG. 4-4 is a front-elevational view of another example of the response assembly of FIG. 4-1 in the form of a telemetry tracking system;

FIG. 4-5 is a top planar view of an additional example of the response assembly of FIG. 4-1 in the form of a touch pad;

FIG. 5-1 is a schematic diagram of a first embodiment of a fifth aspect of the present invention showing a conscious sedation system including a controller and including a response testing apparatus which includes a request assembly and a response assembly;

FIG. 5-2 is a front-elevational view of an example of the response assembly of FIG. 4-1 in the form of a handpiece;

FIG. 5-3 is a schematic diagram of the handpiece (without the band) of FIG. 5-2 including a finger or thumb actuated plunger and including a force sensor;

FIG. 5-4 is a schematic view a different handpiece which includes a resistance sensor;

FIG. 5-5 is a schematic view of a different handpiece which includes a capacitance sensor;

FIG. 5-6 is a schematic view of a different handpiece which includes a compliant air bladder;

FIG. 6-1 is a schematic diagram of a first embodiment of a sixth aspect of the present invention showing a conscious sedation system including a controller and a response testing apparatus, wherein the response testing apparatus includes a request assembly and a response assembly, and wherein the request assembly includes a non-ear-canal-contacting speaker;

FIG. 6-2 is a schematic front elevational view of a first example of the request assembly of FIG. 6-1 including a speaker which communicates the request to the patient at least in part by bone conduction;

FIG. 6-3 is a schematic side elevational view of a second example of the request assembly of FIG. 6-1 including a speaker disposed in a pillow;

FIG. 6-4 is a schematic perspective view of a third example of the request assembly of FIG. 6-1 including a speaker disposed on the outside of a skull cap worn by the patient;

FIG. 6-5 is a schematic perspective view of a fourth example of the request assembly of FIG. 6-1 including a speaker connectable by a sound tube to the outside of a skull cap worn by the patient;

FIG. 6-6 is a cross sectional view of a portion of the skull cap and a portion of the sound tube of FIG. 6-5 connected to the skull cap;

FIG. 7-1 is a schematic diagram of an embodiment of a seventh aspect of the present invention showing a conscious sedation system including a controller having an input for including a personalized message and a response testing apparatus which includes a request assembly and a response assembly;

FIG. 8-1 is a schematic diagram of an embodiment of an eighth aspect of the present invention showing a conscious sedation system including a controller and including a response testing apparatus which includes a request assembly and a response assembly, wherein the response and/or request assembly is a finger movement response assembly;

FIG. 8-2 is an embodiment of a finger movement response assembly in the form of a finger touch response apparatus;

FIG. 8-3 is another embodiment of a finger movement response assembly in the form of a handpiece sensor mechanism;

FIG. 9-1 is a schematic diagram of an embodiment of a ninth aspect of the present invention showing a conscious sedation system including a controller programmed to calibrate a patient's level of hearing and a response testing apparatus which includes a request assembly and a response assembly;

FIG. 9-2 is a block diagram of an embodiment of the method of the present invention using the conscious sedation system involving automated audio calibration;

FIG. 9-3 is a block diagram of another embodiment of the method of the present invention using the conscious sedation system automated audio calibration and determining the level of sedation in a patient; and FIG. 9-4 is a schematic diagram of an embodiment of the present invention showing a response testing apparatus including a sub-controller programmed to calibrate a patient's level of hearing, the response testing apparatus which includes a request assembly and a response assembly.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other aspects, embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described aspects, embodiments, expressions of embodiments, examples, methods, etc. can be combined with any one or more of the other following-described aspects, embodiments, expressions of embodiments, examples, methods, etc. For example, and without limitation, cableless communication can be used in combination with personalized audio requests, etc.

It is also understood that while the following systems, methods, etc. apply to conscious sedation, such systems, methods, etc. have equal application to conscious and unconscious sedation with the appropriate choice of drug(s) and dose rate(s). In one example, such conscious and unconscious sedation system and/or method has the capability to bring the patient into unconscious sedation, to bring the patient into and out of conscious sedation, and/or to assess the patient as the patient moves into and out of deep sedation or consciousness. In one illustration, a deep sedation level or unconsciousness is indicated if a patient response to a stimuli is not detected. Further, the following discussion of conscious sedation also encompasses the conscious sedation portion of a system and/or method which provides both conscious and unconscious sedation. It is noted that conscious sedation includes conscious sedation where the patient is not responsive to stimuli (which is also known as deep sedation) and conscious sedation where the patient is responsive to stimuli.

Conscious Sedation Involving Cableless Communication

Figure 1:
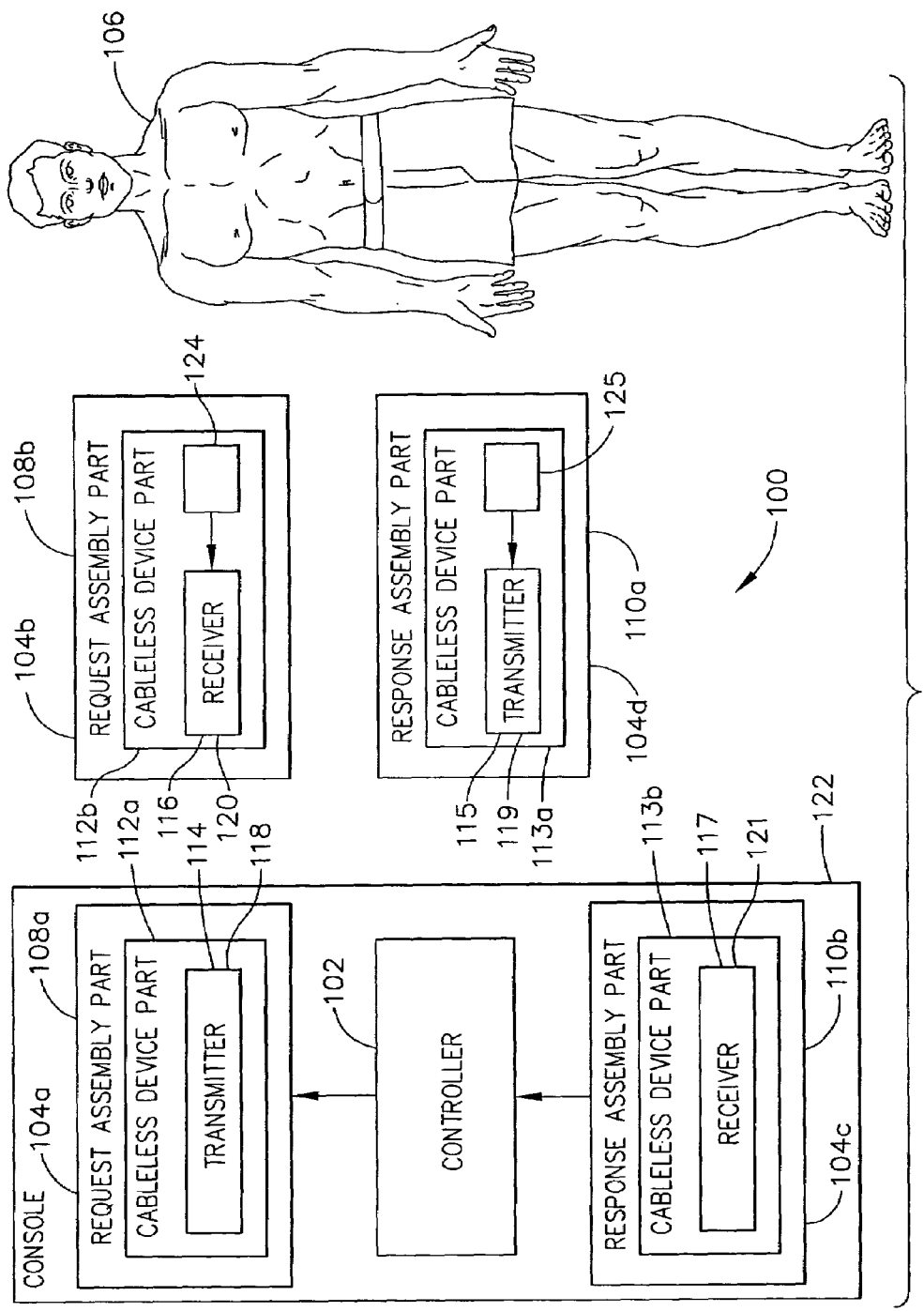
FIG. 1-1 is a schematic diagram of a first embodiment of a first aspect of the present invention showing a conscious sedation system including a controller and including a response testing apparatus which includes a request assembly and a response assembly and which uses cableless communication.

A first aspect of the invention relates to conscious sedation and cableless communication. Referring now to the drawings, FIG. 1-1 illustrates a first embodiment of the first aspect of the invention. A first expression of the first embodiment is for a conscious sedation system 100 including a controller 102 and a response testing apparatus 104 (wherein parts 104a, 104b, 104c and 104d are parts of the response testing apparatus 104). The controller 102 generates a request for a predetermined response from a patient 106 and analyses at least a response made by the patient 106 to the request to determine a level of sedation of the patient 106. The response testing apparatus 104 includes a request assembly 108 (wherein parts 108a and 108b are parts of the request assembly 108) and a response assembly 110 (wherein parts 110a and 110b are parts of the response assembly 110). The request assembly 108 communicates to the patient 106 the request generated by the controller 102. The response assembly 110 senses the response and communicates the response to the controller 102. At least one of the request assembly 108 and the response assembly 110 includes a cableless communication device 112 and 113 (wherein parts 112a and 112b are parts of the cableless communication device 112 and parts 113a and 113b are parts of the cableless communication device 113) which communicates at least one of the request and the response between the controller 102 and the patient 106.

Examples of cableless communication devices 112 and 113 include, without limitation, communication devices using: a radio frequency (RF) transmitter and receiver (such as those operating in the range of 0.1 mega hertz to 3 giga hertz), an ultrasonic transmitter and receiver, an infrared transmitter and receiver, and/or a visible-light transmitter and receiver, etc. Such cableless communication devices are known to the artisan.

In one implementation of the first expression of the embodiment of FIG. 1-1, certain patient vital signs such as blood pressure, blood oxygen saturation (oximetry) and inhalation and exhalation carbon dioxide levels (capnometry) are electronically monitored (not shown in FIG. 1-1) and are also analyzed by the controller 102, in addition to the response from the response assembly 110, to determine a level of sedation of the patient. The term "controller", without limitation, includes one controller and includes two or more spaced-apart subcontrollers, etc.

In one example of the first expression of the embodiment of FIG. 1-1, a user and/or the controller 102 determines a delivery schedule (including any interruption of delivery) of a conscious-sedation drug to the patient 106 based at least in part on the determined level of sedation of the patient 106. The drug delivery apparatus has been omitted from FIG. 1-1 for clarity. A conscious sedation drug is a drug or drug combination which, in an efficacious amount, is capable of sedating the patient 106 during a medical procedure (such as a colonoscopy) while keeping the patient 106 conscious. Conscious sedation drugs, such as Propofol, are well known in the medical art. In one alternative, a user such as a doctor, instead of the controller 102, determines a delivery schedule of the conscious-sedation drug to the patient 106 based at least in part on the determined level of sedation of the patient 106.

In the same or a different example, the cableless communication device 112 and 113 includes a transmitter 114 and 115 and a receiver 116 and 117 in cableless communication with the transmitter, and the cableless communication device 112 and 113 imposes a unique identifier on at least one of the transmitter 114 and 115 and the receiver 116 and 117 which prevents the cableless communication device 112 and 113 from responding to crosstalk from other transmitters. In one illustration, the unique identifier is manually-triggered, is automatically proximity-triggered when the transmitter and the receiver are brought into proximity to each other, or requires both manual and proximity triggering. In one variation, the transmitter 114 and 115 is an RF transmitter 118 and 119, and the receiver 116 and 117 is an RF receiver 120 and 121 in wireless communication with the RF transmitter 118 and 119. In one modification, the cableless communication device 112 and 113 selects the operating frequency of at least one of the RF transmitter 118 and 119 and the RF receiver 120 and 121 which prevents the cableless communication device 112 and 113 from responding to crosstalk from other transmitters. In another modification, the cableless communication device 112 and 113 selects a digital code for at least one of the RF transmitter 118 and 119 and the RF receiver 120 and 121 which prevents the cableless communication device 112 and 113 from responding to crosstalk from other transmitters. In one implementation, the unique identifier is a proximity-triggered unique identifier imposed when the RF transmitter 118 and 119 and the RF receiver 120 and 121 are brought into proximity to each other. In another implementation, the imposing of the unique identifier does not take place automatically with proximity but requires (in addition to proximity manual activation, such as pushing of a push button, to impose the unique identifier. The unique identifier can be erased after a period of inactivity or by manual deactivation at the end of the medical procedure. Such imposing of unique identifiers, including proximity imposing of unique identifiers, is within the capabilities of one of ordinary level of skill in the art. An example of technology which uses proximity imposing of unique identifiers is a gas pump wave card used by drivers at some service stations to pay for gasoline. Alternately, the unique identifiers can be manually set (without regard to proximity). Other techniques to eliminate or reduce crosstalk include reducing the power output of the transmitter such that only a receiver in proximity to the transmitter will respond to the transmitter and/or include directional transmission and/or directional reception.

In one configuration of the first expression of the embodiment of FIG. 1-1, the conscious sedation system 100 also includes a console 122, wherein the controller 102 is disposed in the console 122. In one variation, the console 122 is a procedure room console designed to stay in the medical procedure room. In another variation, the console 122 is a bedside console designed to be transported with the occupied hospital bed to the medical procedure room. In a further variation, the console has a first subconsole designed to stay in the medical procedure room and a second subconsole designed to be a bedside console. It is noted that a bedside console is disposed proximate the patient. In one configuration, the cableless communication takes place directly between a procedure room console and the patient. In another configuration, the cableless communication takes place directly between a procedure room console and a bedside console (with cable communication between the bedside console and the patient). In a further configuration, the cableless communication takes place directly between the bedside console and the patient. Other configurations are left to the artisan.

A second expression of the embodiment of FIG. 1-1 is for a response testing apparatus 104 for a conscious sedation system 100. The response testing apparatus 104 includes a request assembly 108 and a response assembly 110. The request assembly 108 communicates to a patient 106 a request generated by a controller 102 of the conscious sedation system 100 for a predetermined response from the patient 106. The response assembly 110 senses a response made by the patient 106 to the request and communicates the response to the controller 102 which analyses at least the response to determine a level of sedation of the patient 106. At least one of the request assembly 108 and the response assembly 110 includes a cableless communication device 112 and 113 which communicates at least one of the request and the response between the controller 102 and the patient 106.

In one example of the second expression of the embodiment of FIG. 1-1, the request assembly 108 includes a cableless communication device 112 which communicates the request from the controller 102 to the patient 106. In one variation, the cableless communication device 112 includes an RF transmitter 118 and includes an RF receiver 120 in wireless communication with the RF transmitter 118 and disposed proximate the patient 106. In one modification, the request assembly 108 verifies that the request was received by the RF receiver 120 (such as by using an accelerometer or a switch indicating a request in the form of vibration from a vibrator has been received or such as by using a microphone indicating a request in the form of a sound from a speaker has been received and sending a verification signal back to the controller) as is within the capabilities of the artisan. In the same or a different modification, the request assembly 108 includes a battery-operated portion 124, and the request assembly 108 monitors the battery condition of the battery-operated portion 124. It is noted that the term "battery" includes a cell and a series of cells.

Figures 1, 2:
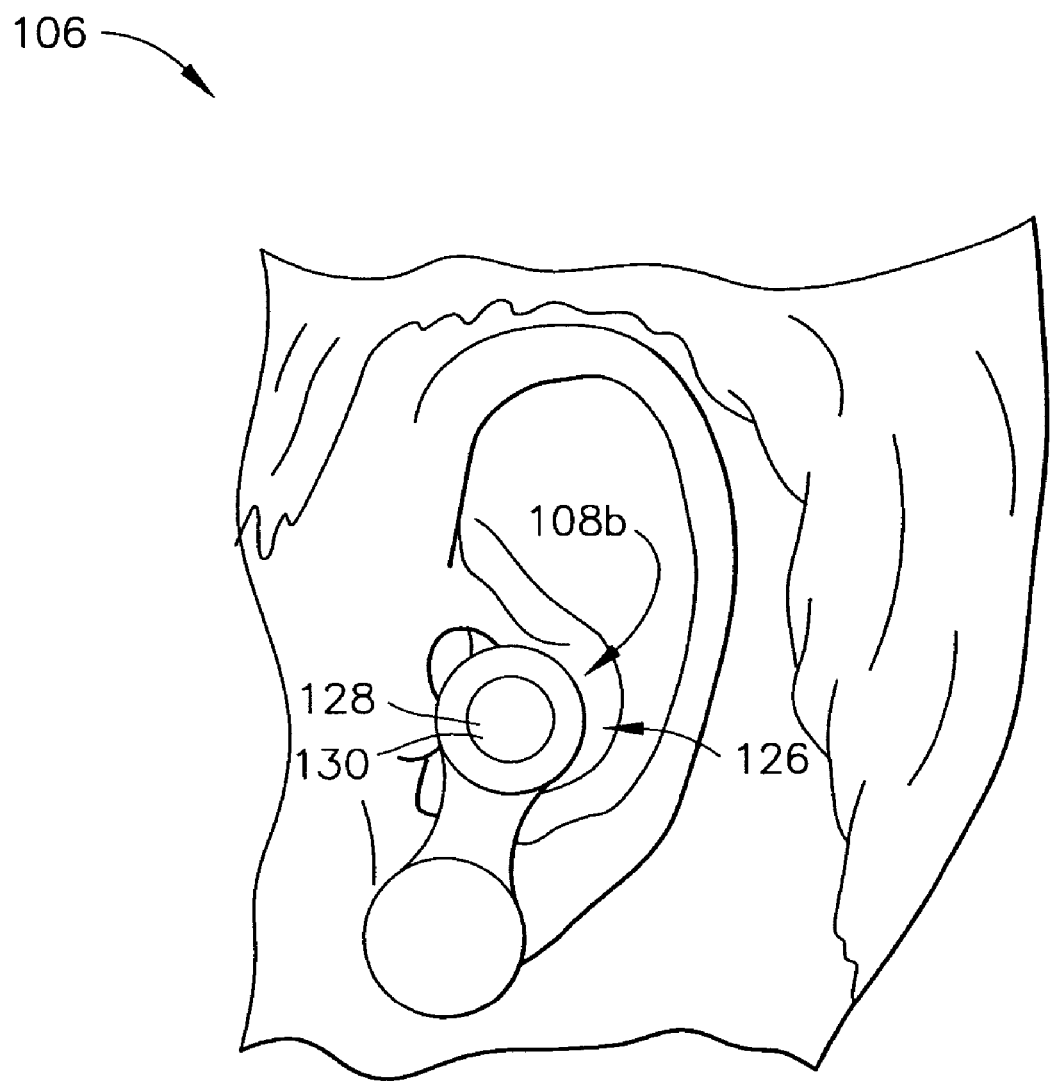

In one implementation of the request assembly 108, the request assembly 108 is an auditory request assembly 126 as shown in FIG. 1-2. The audible request assembly 126 includes a speaker 128, and the RF receiver 120 (omitted from FIG. 1-2 for clarity) is used to activate the speaker 126 to produce an audible request to the patient 106. In one variation, the speaker 128 is an earphone 130 (such as one which clips on an ear lobe) disposable proximate an ear of the patient 106. In one modification, the RF receiver 120 is disposed within or on the earphone housing. In another modification, the RF receiver is disposed on a headset and the RF receiver is wired to the earphone which is supported by the headset.

Figures 1, 2, 3, 4:
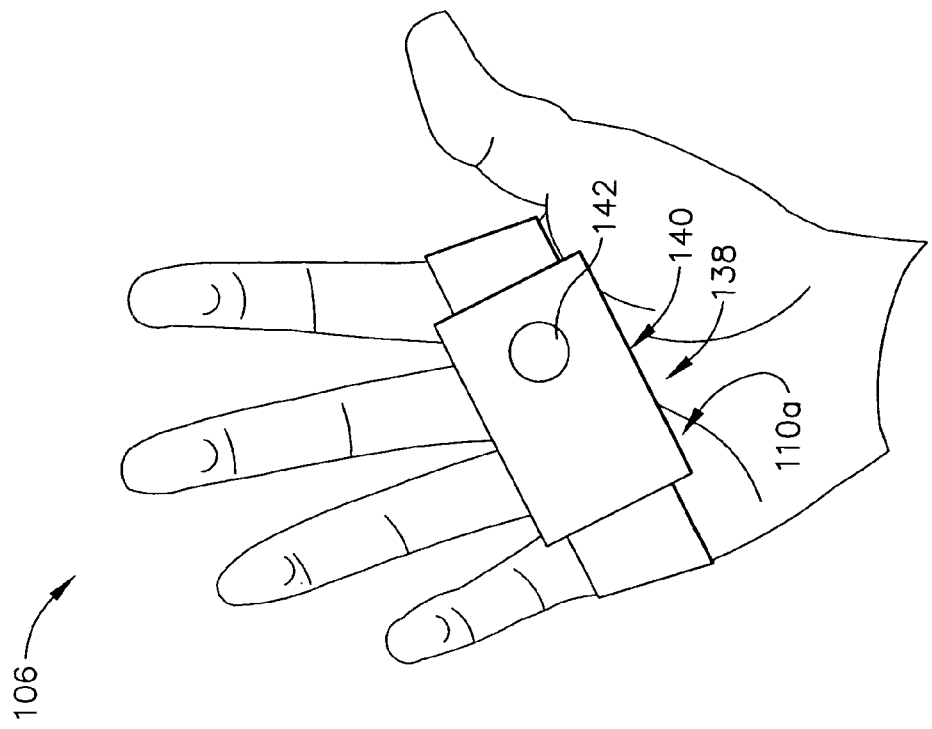
Figures 1, 2, 3:
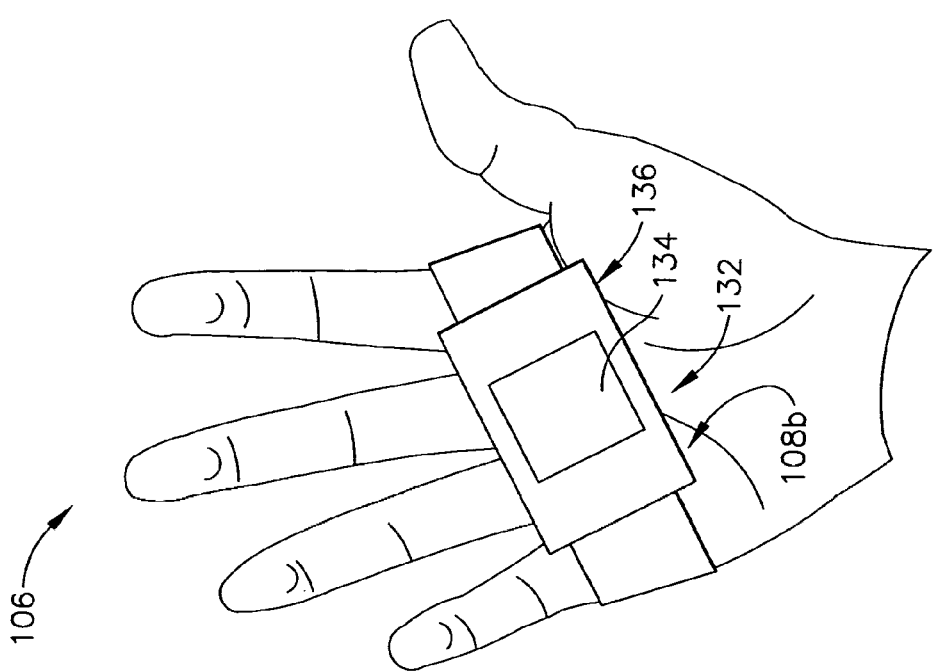

In another implementation of the request assembly 108, the request assembly 108 is a vibratory request assembly 132 as shown in FIG. 1-3. The vibratory request assembly 132 includes a vibrator 134, and the RF receiver 120 (omitted from FIG. 1-3 for clarity) is used to activate the vibrator 134 to produce a tactile request to the patient 106. In one variation, the vibrator 134 is disposed in a handpiece 136, and the handpiece 136 is disposable proximate a hand of the patient 106.

In the same or a different example of the second expression of the embodiment of FIG. 1-1, the response assembly 110 includes a cableless communication device 113 which communicates the response from the patient 106 to the controller 102. In one variation, the cableless communication device 113 includes a transmitter 115 which is an RF transmitter 119 disposed proximate the patient 106 and includes a receiver 117 which is an RF receiver 121 in wireless communication with the RF transmitter 119. In one modification, the response assembly 110 verifies that the response was received by the RF receiver 121 as is within the capabilities of the artisan. In the same or a different modification, the response assembly 110 includes a battery-operated portion 125, and the response assembly 110 monitors the battery condition of the battery-operated portion 125.

In one implementation of the response assembly 110, the response assembly 110 is a switch response assembly 138 as shown in FIG. 1-4. The switch response assembly 138 includes a handpiece 140 disposable proximate a hand of the patient 106. The handpiece 140 includes a switch 142, and the response includes the patient 106 activating the switch 142 whereby a signal is sent by the RF transmitter 119 (omitted from FIG. 1-4 for clarity). In one variation, the handpiece 140 and the handpiece 136 are the same handpiece which includes both the vibrator 134 and the switch 142.

In one configuration of the second expression of the embodiment of FIG. 1-1, the request assembly 108 includes a cableless communication device 112 which communicates the request from the controller 102 to the patient 106, and the response assembly 110 includes a cableless communication device 113 which communicates the response from the patient 106 to the controller 102. In one variation, the transmitter 114 of the cableless communication device 112 of the request assembly 108 is disposed on or in the console 122, and the receiver 117 of the cableless communication device 113 of the response assembly 110 is disposed on or in the console 122.

A third expression of the embodiment of FIG. 1-1 is a response testing apparatus 104 for a conscious sedation system 100. The response testing apparatus 104 includes a request assembly 108 and a response assembly 110. The request assembly 108 communicates to a patient 106 a request generated by a controller 102 of the conscious sedation system 100 for a predetermined response from the patient 106. The response assembly 110 senses a response made by the patient 106 to the request and communicates the response to the controller 102 which analyses at least the response to determine a level of sedation of the patient 106. At least one of the request assembly 108 and the response assembly 110 includes a cableless communication device 112 and 113 which communicates at least one of the request and the response between the controller 102 and the patient 106. The cableless communication device 112 and 113 includes a transmitter 114 and 115 and a receiver 116 and 117 in cableless communication with the transmitter 114 and 115. The cableless communication device 112 and 113 imposes a unique identifier on at least one of the transmitter 114 and 115 and the receiver 116 and 117 which prevents the cableless communication device 112 and 113 from responding to crosstalk from other transmitters.

In one example of the third expression of the embodiment of FIG. 1-1, the unique identifier (which in one option includes the serial number of one or more components) is a proximity-triggered unique identifier imposed when the transmitter 114 and 115 and the receiver 116 and 117 are brought into proximity to each other. In one variation, the transmitter 114 and 115 is an RF transmitter 118 and 119, and the receiver 116 and 117 is an RF receiver 120 and 121 in wireless communication with the RF transmitter 118 and 119. In one modification, the cableless communication device 112 and 113 selects the operating frequency of at least one of the transmitter 114 and 115 and the receiver 116 and 117 which prevents the cableless communication device 112 and 113 from responding to crosstalk from other transmitters. In another modification, the cableless communication device 112 and 113 selects a digital code for at least one of the transmitter 114 and 115 and the receiver 116 and 117 which prevents the cableless communication device 112 and 113 from responding to crosstalk from other transmitters. In one application, the user verifies that the imposition of the unique identifier has been successful before use with a patient. In one variation, there is also included a lockout which prevents use of the cableless communication device unless the imposition of the unique identifier has been successfully verified.

Advantages and benefits of one or more of the expressions of the embodiment of FIG. 1-1 include elimination of cables in the medical procedure room which allows the medical procedure (including surgery) to be performed with less wiring clutter between the patient 106 and the console 122. Cableless communication means the patient is less likely to become entangled in cords and means greater reliability due to fewer connections. Cableless communication provides for easier user setup as no cable connections need be made. It is noted that it is easier to design equipment to meet electrical safety requirements using cableless communication than using cables. In the unique identifier example, imposing unique identifiers allows, in one implementation, any handpiece 136 and 140 to be used with any console 122.

Conscious Sedation Involving a Cannula

A second aspect of the invention relates to conscious sedation and involves a cannula. A cannula is a well known medical device which is used for monitoring the breathing of a patient and which is placed on the face of the patient proximate the nose and/or mouth of the patient. Referring now to the drawings, FIG. 2-1 illustrates a first embodiment of the second aspect of the invention. A first expression of the first embodiment is for a conscious sedation system 200 including a controller 202, a cannula 204, and a response testing apparatus 206 (wherein parts 206a and 206b are parts of the response testing apparatus 206). The controller 202 generates a request for a predetermined response from a patient 208 and analyses at least a response made by the patient 208 to the request to determine a level of sedation of the patient 208. The cannula 204 is disposable on the face of the patient 208 proximate at least one of the nose and the mouth of the patient 208 for monitoring the breathing of the patient. The response testing apparatus 206 includes a request assembly 210 and a response assembly 212. The request assembly 210 communicates to the patient 208 the request generated by the controller 202. The response assembly 212 senses the response and communicates the response to the controller 202. At least a part of at least one of the request and response assemblies 210 and 212 is supported by the cannula 204. The terminology "supported by the cannula" means supported at least in part by the cannula.

An example of a cannula 204 is shown in FIG. 2-2 wherein the cable/tube 214 operatively connecting the cannula 204 to the controller 202 has been removed. The headband 216 of the cannula 204 is used to secure the cannula 204 on the face of the patient 208. In one use, the cannula 204 is used to monitor the inhalation and exhalation carbon dioxide levels (capnometry) of the patient 208 and/or the pressure of the patient's inhalation and exhalation and optionally delivers oxygen to the patient. It is noted that at least a part of the request assembly 210 is supported by the cannula 204 in the first embodiment shown in FIG. 2-1.

In one implementation of the first expression of the embodiment of FIG. 2-1, certain patient vital signs such as blood pressure, blood oxygen saturation (oximetry) and inhalation and exhalation carbon dioxide levels (capnometry) are electronically monitored and are also analyzed by the controller 202, in addition to the response from the response assembly 212, to determine a level of sedation of the patient. The term "controller", without limitation, includes one controller and includes two or more spaced-apart subcontrollers, etc. An example of a response assembly 212 in FIG. 2-1 is a handpiece which has a switch and which is secured to the hand of the patient 208. Other examples include a chest band to monitor a deep breath.

In one example of the first expression of the embodiment of FIG. 2-1, a user and/or the controller 202 determines a delivery schedule (including any interruption of delivery) of a conscious-sedation drug to the patient 208 based at least in part on the determined level of sedation of the patient 208. The drug delivery apparatus has been omitted from FIG. 2-1 for clarity. A conscious sedation drug is a drug or drug combination which, in an efficacious amount, is capable of sedating the patient 208 during a medical procedure (such as a colonoscopy) while keeping the patient 208 conscious. Conscious sedation drugs, such as Propofol, are well known in the medical art. In one alternative, a user such as a doctor, instead of the controller 202, determines a delivery schedule of the conscious-sedation drug to the patient 208 based at least in part on the determined level of sedation of the patient 208.

In the same or a different example, the request assembly 210 includes a first vibrator 218 supported by the cannula 204. In one variation, the first vibrator 218 produces a tactile request to the face of the patient 208. In one modification, the first vibrator 218 is disposed in the cannula 204. The terminology "disposed in the cannula" means disposed at least in part in the cannula. In a different modification, the first vibrator 218 is disposed on the cannula 204. In one arrangement, the request assembly 210 includes a second vibrator 220 disposable to produce a tactile request to a site on the patient 208 other than to the face of the patient 208. In one application, the controller 202 at least compares responses of the patient to tactile requests from the first and second vibrators 218 and 220 in determining the level of sedation of the patient. In another arrangement, the first vibrator 218 is the only vibrator of the request assembly 210 producing a tactile request.

A second embodiment of the second aspect of the present invention is for a conscious sedation system 222 and is shown in FIGS. 2-3 and 2-4. In a first expression of the second embodiment, the conscious sedation system 222 includes a controller 224, a cannula 226, and a response testing apparatus 228 (wherein parts 228a and 228b are parts of the response testing apparatus 228). The response testing apparatus 228 includes a request assembly 230 and includes a response assembly 232. At least a part of the response assembly is supported by the cannula 226.

In one implementation of the second embodiment, the predetermined response is a patient 208 head-generated response. In one variation, the patient 208 head-generated response is a patient-generated vocal response, and the response assembly 232 includes a sound detector 234 (such as a microphone) supported by the cannula 226. In one modification, the controller 224 at least uses at least one of the intensity and the tonal qualities of the vocal response in determining the level of sedation of the patient 208. In another variation, the patient 208 head-generated response is a patient-generated head movement response, and the response assembly 232 includes a motion sensor 236 supported by the cannula 226. In a further variation, the patient 208 head-generated response is a patient-generated breathing response, and the response assembly 232 includes a breathing sensor 238 (such as a pressure sensor) and/or a breathing-detection tube supported by the cannula 226. In one illustration employing a breathing-detection tube, the breathing sensor is operatively connected to the tube and is located remote from the cannula. In one modification, the patient-generated breathing response includes at least one of a yawn and a breath deeper than an immediate previous breath. In the same or a different modification, the breathing sensor 238 detects the pressure of the exhaled breathing of the patient 208. Examples of request assemblies 230 in FIG. 2-3 include a handpiece having a vibrator and secured to the hand of the patient 208 and an earphone speaker disposed in the ear of the patient 208. Other request assemblies include vibrators supported by a blood pressure cuff, supported by a pulse oximeter disposable on a finger or ear lobe of the patient, or supported by another medical device. Additional request assemblies include vibrators placed upon the face, head, neck, or upper spine of the patient.

In one configuration, not shown, the cannula supports at least a part of the request assembly and at least a part of the response assembly. In one example, the first vibrator 218 and at least one of the sound detector 234, the motion sensor 236, and the breathing sensor 238 are supported by the same cannula.

An alternate expression of either or both of the first and second embodiments of the second aspect of the invention, which will be described for simplicity using only the part numbers of the first embodiment of FIG. 2-1, is for a cannula and response testing assemblage 240 (wherein parts 240*a* and 240*b* are parts of the response testing assemblage 240) for a conscious sedation system 200. The cannula and response testing assemblage 240 includes a cannula 204 and includes a response testing apparatus 206. The cannula 204 is disposable on the face of a patient 208 proximate at least one of the nose and the mouth of the patient 208 for monitoring the breathing of the patient. The response testing apparatus 206 includes a request assembly 210 and a response assembly 212. The request assembly 210 communicates to the patient 208 a request generated by a controller 202 of the conscious sedation system 200 for a predetermined response from the patient 208. The response assembly 212 senses a response made by the patient 208 to the request and communicates the response to the controller 202 which analyses at least the response to determine a level of sedation of the patient 208. At least a part of at least one of the request and response assemblies 210 and 212 is supported by the cannula 204.

In one example of the cannula and response testing assemblage 240, the request assembly includes a first vibrator 218 supported by the cannula 204. In the same or a different example, the response is a patient 208 head-generated response, and at least a part of the response assembly is supported by the cannula. In one variation, the response assembly includes at least one of a sound detector, a motion sensor, a breathing sensor, and a breathing-detection tube supported by the cannula.

A third embodiment of the second aspect of the present invention is for a conscious sedation system 242 and is shown in FIG. 2-5. The conscious sedation system 242 includes a controller 244 and a response testing apparatus 246 (wherein parts 246*a* and 246*b* are parts of the response testing apparatus 246). The controller 244 generates a request for a predetermined breathing response from a patient 208 and analyses at least a breathing response made by the patient 208 to the request to determine a level of sedation of the patient 208. The response testing apparatus 246 includes a request assembly 248 and a cannula 250. The request assembly 248 communicates to the patient 208 the request generated by the controller 244. The cannula 250 is disposable on the face of the patient 208 proximate at least one of the nose and the mouth of the patient 208 for monitoring the breathing of the patient 208, wherein the cannula 250 is operatively connected to the controller 244.

In one example of the third embodiment, a user and/or the controller 244 determines a delivery schedule (including any interruption of delivery) of a conscious-sedation drug to the patient 208 based at least in part on the determined level of sedation of the patient 208.

It is noted that unnumbered lines in the figures which emanate from the controller 202, 224, and 244 are connecting cables/tubes as is understood by those skilled in the art.

In one employment, the controller analyses the sound intensity and/or tonal qualities of the sound response for use in determining the level of sedation of the patient. Examples include predetermined vocal sounds which include one or more words, phrases, sighs, yawns, groans, etc. Baseline vocal sound responses from the patient before the start of sedation may be used to train the controller 244 to recognize vocal sound responses from the patient before and during patient sedation. Advantages of a vocal sound response include such a response being easier to make for a more deeply sedated patient than activating a switch on a handpiece. Also, some patients due to infirmity, physical handicap, etc. may be able to make a vocal response but be unable to activate a switch on a handpiece.

Advantages and benefits of one or more of the expressions of the embodiments of FIGS. 2-1 to 2-5 include elimination of an independent support for at least a part of the request assembly and/or the response assembly of the response testing apparatus by making dual use of the cannula when a cannula is used in a conscious sedation system. In the vibrator request example, a vibratory tactile request to the face of a patient is easier for a more deeply sedated patient to perceive (as the face is more sensitive to touch) than a vibratory tactile request to the hand of a patient. In the patient head-generated response example, a patient made sound, head movement, or breathing response to a request from the controller is easier for a more deeply sedated patient to make than activating a switch on a handpiece.

In an expansion of the second aspect of the invention, the response is a patient made vocal sound, and the response assembly is not limited to being supported by the cannula. In this expanded second aspect of the invention, the sound detector need only be able to detect patient made vocal sounds. The type of sound detector is left to the artisan. In one example, a microphone is disposable proximate the mouth of the patient. In one application, the microphone is disposed on the hospital bed proximate the face of the patient. In another application, the microphone is disposed on a bedside stand. In a further application, the microphone is disposed on the patient or the patient's hospital gown. Other applications are left to the artisan. In another example, a sound tube extends from proximate the patient's face to a remotely-located sound detector. In a further example, the microphone picks up patient made sounds by bone conduction. Other examples are left to the artisan.

Time Variant Vibration Stimulus Response for a Conscious Sedation System

A third aspect of the invention relates to conscious sedation and the application of discrete vibration pulses to determine the level of sedation in a patient. The invention is a system and method of applying discrete vibration pulses and altering the time intervals between pulses and the duration of the pulses to determine the level of sedation in a patient. In the prior art, the level of sedation in a patient is determined by applying a vibration stimuli to the sedated patient and assessing the patient's response to the stimuli. If the patient does not respond, the intensity of the stimuli is increased until the patient responds to the stimuli. The intensity of the stimuli required to generate the patient's response is correlated with the patient's level of sedation. One disadvantage in this method is that the level of intensity required to generate a response from the patient may be extremely high. In the case of a handpiece, the vibration stimuli may be so intense that it is difficult for the sedated patient to hold onto to, let alone, respond to the stimuli by squeezing the handpiece.

Accordingly, in one embodiment of the present invention, a method for determining the level of sedation in a patient utilizes the time interval of the vibration stimuli thereby obviating the need to use the intensity stepping approach used in the prior art. In essence, the patient's ability to discern vibratory time-dependent patterns can be used to determine the patient's level of sedation. For example, in a time interval analysis, a set of vibration stimuli comprises several vibratory pulses which are applied to the patient with a predetermined time interval between each pulse. When the patient is not sedated or less sedated, the patient may be able to discern the distinct pulses, whereas when the patient is more sedated, the patient's ability to discern distinct pulses may be reduced. Referring to FIG. 3-1, a sample set of three pulses is applied with a predetermined time spaced in between each pulse. The time between the first pulse and the second pulse is T1 and the between the second pulse and third pulse is T2. A less sedated patient may be able to discern the three individual pulses, whereas when the patient becomes more sedated, he may only recognize two of the three pulses because of the reduced ability to discern the time interval spaced between the pulses. Further, when the patient becomes even more sedated, his ability to discern the time interval spaced between the pulses may be reduced to the extent that the patient is only able to discern the set of three pulses as one whole pulse. Thus, this ability to discern the time interval between each distinct pulse correlates with the patient's level of sedation. As the patient becomes more sedated, the greater the time interval is required between each pulse for the patient to discern the distinct pulses. Accordingly, the time intervals between the pulses of each set of stimuli may be modified to be greater or less for subsequent sets to analyze the patient's response to the sets and to correlate the response to the patient's level of sedation. Although the time interval ranges will vary with the patient, the interval may range from 0.05 to 15.0 seconds. More typically, the interval ranges from 0.3 to 1.0 seconds. In one embodiment of the invention, the range is 0.5 to 0.7 seconds. In one typical protocol that might be used to monitor sedation, the time interval between each pulse may be initiated at about 0.4 seconds. If the patient detects the distinct pulses, the time interval between the pulses is decreased to 0.2 seconds. If the patient does not detect the distinct pulses, the time interval between the pulses is increased to 0.6 seconds.

In another embodiment of the present invention, a method for determining the level of sedation in a patient utilizes the duration of the pulses of the vibration stimuli thereby obviating the need to use the intensity stepping approach used in the prior art. Referring to FIG. 3-2, the vibration set contains three vibratory pulses, wherein each pulse has a predetermined duration D1, D2 and D3. The duration of the pulses in each set can be the same or different and can be modified to be greater or less in subsequent sets. In essence, the patient's ability to discern the duration of the vibratory pulses can be used to determine the patient's level of sedation. For instance, a pulse that is 0.5 second in duration may be recognized by a patient who is not sedated or less sedated but when the patient becomes more sedated, he may not be able to discern the 0.5 second pulse stimuli but may instead require a pulse with a longer duration, such as a one second pulse, in order to discern it. Accordingly, the patient's ability to discern a pulse with a prescribed duration can be used to assess the patient's level of sedation. The greater the duration of the pulse necessary for the patient to discern the pulse, the more sedated the patient. In a more preferred embodiment of the invention, the vibratory pulse is a "crisp" or sharp pulse; crisp pulses are more alerting and stimulating and are more able to evoke a response from the sedated patient. In the prior art, after the vibratory pulse is applied, the pulse glides to a halt, i.e. gradually decreasing from its highest intensity to its lowest intensity. However, in the present invention, the pulses that are applied are sharp pulses that come to a halt almost immediately, wherein the time it takes to go from its highest intensity to its lowest intensity is about 0.1 second. This is achieved by employing a braking device such as an electrical brake or a brake clutch to provide prompt cessation. Furthermore, the time it takes for the pulse to go from its lowest intensity to its highest intensity is less than about 0.1 second. This enables the request unit to send a crisp pulse of a predetermined duration to assess the patient's level of sedation. Although the duration ranges of the pulses will vary with the patient, the duration may range from 0.1 to 15 seconds. More typically, the duration ranges from 0.5 to 1.0 seconds. In one embodiment of the invention, the range is 0.5 to 1.0 second. In one typical protocol that might be used to monitor sedation, the duration of each pulse may be initiated at about 0.6 second. If the patient detects the distinct pulses, the duration of the pulses is decreased to 0.4 second. If the patient does not detect the distinct pulses, the duration between the pulses is increased to 0.9 second.

In another manifestation of the invention, both the time interval and the duration of the pulse sets may be used in conjunction to assess the patient's response and determine the level of sedation of the patient. A set of vibration stimuli comprising vibratory pulses of predetermined duration for each pulse and predetermined time intervals between each pulse is applied to the patient. The patient then responds to the set of vibration stimuli. A subsequent set of vibration stimuli can be applied to generate a subsequent response by the patient. The subsequent set of vibration stimuli can be the same or modified from the previous set by either altering the duration and/or time interval. In yet a further embodiment of the invention, the individual vibratory pulses can be intensity modulation or frequency modulation pulses. More specifically, an intensity modulation pulse is a vibratory pulse that has a variable intensity within the individual pulse itself. A frequency modulation pulse is a vibratory pulse that has a variable frequency within the individual pulse itself. Either intensity and frequency modulation pulses may be incorporated with the time interval between and/or duration of the pulses in order to assess the level of sedation of a patient. An embodiment of a method of the invention as shown in FIG. 3-4 comprises applying a first stimuli to a patient who has received, is receiving or is about to receive a conscious sedation drug, instructing the patient to respond to the stimuli, monitoring a patient's response to the stimuli, applying an additional stimuli to the patient when the patient has received, is receiving or is about to receive a dose of a conscious sedation drug, wherein the additional stimuli can be the same or different as the first stimuli, monitoring the patient's response to the additional stimuli, repeating the steps of applying the additional stimuli and monitoring the patient's response to the additional stimuli to determine the patient's level of sedation. Furthermore, the patient's initial or previous response may be used as a baseline for comparison to the present response.

Note that FIGS. 3-1 and 3-2 are only examples vibration sets; the vibration sets can contain any number of pulses and the time interval between each of the pulses T1, T2 and so forth and the duration of each pulse D1, D2 and so forth can be the same or different and adjusted to greater or less in subsequent sets of vibration stimuli to determine the level of sedation of the patient.

Referring to the drawings, FIG. 3-3 illustrates yet another embodiment of the third aspect of the invention. The embodiment is for a conscious sedation system 300 including a controller 302 and a response testing apparatus 304. The controller generates a request for a predetermined response from a patient 306, the request comprising a vibration stimuli set having a vibratory pulses having predetermined time interval(s) between each of the pulses and predetermined duration(s) for each pulse. The controller analyses at least a response generated by the patient 306 to the request to determine a level of sedation of the patient 306. The response testing apparatus 304 includes a request assembly 308 and a response assembly 310. The request assembly 308 communicates to the patient 306 the request generated by the controller 302.

In one implementation of the embodiment of FIG. 3-3, certain patient vital signs such as blood pressure, blood oxygen saturation (oximetry) and inhalation and exhalation carbon dioxide levels (capnometry) are electronically monitored and are also analyzed by the controller 302, in addition to the response from the response assembly 310, to determine a level of sedation of the patient. The term "controller", without limitation, includes one controller and includes two or more spaced-apart subcontrollers, etc. Examples of request assemblies 308 in FIG. 3-3 include a handpiece having a vibrator and secured to the hand of the patient 306 and an earphone speaker disposed in the ear of the patient 306. Other request assemblies include vibrators supported by a blood pressure cuff, supported by a pulse oximeter disposable on a finger or ear lobe of the patient, or supported by another medical device. Additional request assemblies include vibrators placed upon the face, head, neck, or upper spine of the patient.

In one example of the expression of the embodiment of FIG. 3-3, the controller 302 determines a delivery schedule of a conscious sedation drug to the patient 306 based at least in part on the determined level of sedation of the patient 306. The drug delivery apparatus has been omitted from FIG. 3-3 for clarity. A conscious sedation drug is a drug or drug combination which, in an efficacious amount, is capable of sedating the patient 306 during a medical procedure (such as a colonoscopy) while keeping the patient 306 conscious. Conscious sedation drugs, such as Propofol, are well known in the medical art. In one alternative, a doctor, instead of the controller 302, determines a delivery schedule of the conscious sedation drug to the patient 306 based at least in part on the determined level of sedation of the patient 306 i.e. as determined by the described embodiments.

Conscious Sedation Involving a Hand Motion Patient Response

A fourth aspect of the invention relates to conscious sedation and involves a hand motion patient response. Referring now to the drawings, FIG. 4-1 illustrates a first embodiment of the fourth aspect of the invention. A first expression of the first embodiment is for a conscious sedation system 400 including a controller 402 and a response testing apparatus 404 (wherein parts 404a and 404b are parts of the response testing apparatus 404). The controller 402 generates a request for a predetermined hand motion response from a patient 406 and analyses at least a hand motion response made by the patient 406 to the request to determine a level of sedation of the patient 406. The response testing apparatus 404 includes a request assembly 408 and a response assembly 410. The request assembly 408 communicates to the patient 406 the request generated by the controller 402. The response assembly 410 senses the hand motion response and communicates the hand motion response to the controller 402.

By "hand motion" is meant translation and/or rotation of a hand of the patient 406. In some applications of the fourth aspect of the invention, hand motion is translation and/or rotation of the palm of the hand. Such palm motion may or may not be accompanied by movement of one or more fingers and/or thumb relative to the palm of the hand. In one variation, such palm motion is substantially without any finger/thumb movement relative to the palm. Examples of body movement of a patient 406 undergoing conscious sedation which results in, or can result in, hand motion include, without limitation, bending of the wrist, rotation of the forearm, bending of the elbow, and motion of the upper arm.

In one implementation of the first expression of the embodiment of FIG. 4-1, certain patient vital signs such as blood pressure, blood oxygen saturation (oximetry) and inhalation and exhalation carbon dioxide levels (capnometry) are electronically monitored and are also analyzed by the controller 402, in addition to the response from the response assembly 410, to determine a level of sedation of the patient. The term "controller", without limitation, includes one controller and includes two or more spaced-apart subcontrollers, etc. Examples of request assemblies 408 in FIG. 4-1 include a handpiece having a vibrator and secured to the hand of the patient 406 and an earphone speaker disposed in the ear of the patient 406. Other request assemblies include vibrators supported by a blood pressure cuff, supported by a pulse oximeter disposable on a finger or ear lobe of the patient, or supported by another medical device. Additional request assemblies include vibrators placed upon the face, head, neck, or upper spine of the patient. In one design, a cable 412 operatively connects the controller 402 to the request assembly 408, and a cable 414 operatively connects the response assembly 410 to the controller 402.

In one example of the first expression of the embodiment of FIG. 4-1, a user and/or the controller 402 determines a delivery schedule (including any interruption of delivery) of a conscious-sedation drug to the patient 406 based at least in part on the determined level of sedation of the patient 406. The drug delivery apparatus has been omitted from FIG. 4-1 for clarity. A conscious sedation drug is a drug or drug combination which, in an efficacious amount, is capable of sedating the patient 406 during a medical procedure (such as a colonoscopy) while keeping the patient 406 conscious. Conscious sedation drugs, such as Propofol, are well known in the medical art. In one alternative, a user such as a doctor, instead of the controller 402, determines a delivery schedule of the conscious-sedation drug to the patient 406 based at least in part on the determined level of sedation of the patient 406.

A first example of the response assembly 410 includes a handpiece 416, as shown in FIG. 4-2, wherein the handpiece 416 sends a signal to the controller 402 when the handpiece 416 is moved. In one application, the handpiece 416 is attachable to the hand of the patient 406, such as through use of a band 418. In one variation, the handpiece 416 includes at least one accelerometer 420, 422 and 424 as shown in FIG. 4-3. In one modification, the handpiece 416 includes three mutually-orthogonal accelerometers 420, 422 and 424 or tilt sensors. In one usage, the predetermined hand motion response is a jiggle/shake of the handpiece of a predetermined distance, velocity and/or acceleration. In another usage, the predetermined hand motion response is a movement of the handpiece along a predetermined path and, optionally, at a predetermined velocity and/or acceleration at points along the predetermined path.

In one implementation of the handpiece 416, the controller 402 analyzes at least the position and/or orientation and/or changes therein of the handpiece 416 to determine the level of sedation of the patient 406. In the same or a different implementation, the controller 402 analyzes at least the velocity of the handpiece 416 to determine the level of sedation of the patient 406. In the same or a different implementation, the controller 402 analyzes at least the acceleration of the handpiece 416 to determine the level of sedation of the patient 406. In one variation, the controller 402 analyzes at least two of the position, the velocity, and the acceleration of the handpiece 416 to determine the level of sedation of the patient 406. In one modification, the controller 402 analyzes at least the position, the velocity, and the acceleration of the handpiece 416 to determine the level of sedation of the patient 406. In one application, the controller 402 creates a time path of the movement of the handpiece 416 and compares the deviation of that time path from a predetermined time path of the predetermined hand motion response to determine the level of sedation of the patient 406.

In one construction of the handpiece 416, the handpiece 416 includes other types of motion sensors or position sensors in place of or in addition to an accelerometer-type of motion sensor. Such other motion sensors include tilt sensors, micromachined gyroscopes, compasses, etc. Such other position sensors include a telemetry transponder, etc.

In one employment of the first expression of the embodiment of FIG. 4-1, the predetermined hand motion response is the patient 406 moving a hand toward another part of the body. In one variation, the hand (such as the hand including an extended finger) is moved toward the nose. In one modification, the response assembly 410 includes a proximity sensor (not shown) which sends a signal to the controller 402 when the distance between the hand (such as the distance of the extended finger of the hand) and the nose is within a predetermined distance. Such signal is used by the controller to indicate that the patient 406 is at a level of consciousness defined, at least in part, by the predetermined "hand-to-body-part" hand motion response. In a different employment, the predetermined hand motion response is the patient 406 moving a hand (such as the hand including an extended finger) to trace out a figure such as the figure "8". In one modification, the response assembly 410 includes one or more accelerometers 420, 422 and 424 whose output(s) is used by the controller 402 in determining if the hand motion response is close enough to the predetermined hand motion response to indicate that the patient 406 is at a level of consciousness defined, at least in part, by the predetermined "figure-tracing" hand motion response.

In one combination of hand motion requests, the controller 402 makes two requests. One request is for the patient 406 to move a hand toward another part of the body. The other request is for the patient 406 to move a hand to trace out a figure. The controller 402 at least analyzes the responses from the two requests to determine the level of sedation of the patient. In one example, a patient who passes the "figure-tracing" request but fails the "finger-to-body-part" request is considered by the controller 402 (with other inputs used by the controller for determining the level of sedation being equal) to be at a deeper level of sedation than a patient who passes both requests.

In an expansion of the fourth aspect of the invention, the response is not limited to a hand motion response but includes a series of requests for different types of predetermined responses. In one employment, such series is in an ascending or a descending order of difficulty for a patient to give an acceptable (i.e., acceptable as determined by the controller 402) response. The acceptable response for different types of predetermined responses corresponds (with other inputs used by the controller for determining the level of sedation being equal) to different levels of sedation of the patient. One example of such a series includes requests for: "figure tracing", "hand-to-body-part", switch activation on a handpiece within a predetermined time since the request, double-clicking a button on a handpiece within a predetermined time interval, and any movement of a handpiece. Other examples are left to the artisan.

A second expression of the embodiment of FIG. 4-1 is for a conscious sedation system 400 including a controller 402 and a response testing apparatus 404. The controller 402 generates a request for a predetermined hand motion response from a patient 406, analyses at least a hand motion response made by the patient 406 to the request to determine a level of sedation of the patient 406, and generates a feedback signal which is communicated (in one example by a "clicker" 426 in the handpiece 416) to the patient 406 when the hand motion response from the patient 406 meets a predetermined criteria. The response testing apparatus 404 includes a request assembly 408 and a response assembly 410. The request assembly 408 communicates to the patient 406 the request generated by the controller 402. The response assembly 410 senses the hand motion response and communicates the hand motion response to the controller 402.

In one example of the second expression of the embodiment of FIG. 4-1, the controller 402 changes the predetermined criteria between two requests and at least analyzes the responses from the two requests to determine the level of sedation of the patient 406. For example, a patient 406 who passes a two-inch proximity criteria for a hand to nose request but fails a one-inch proximity criteria is considered by the controller 402 (with other inputs used by the controller for determining the level of sedation being equal) to be at a deeper level of sedation than a patient who passes both criteria.

A third expression of the embodiment of FIG. 4-1 is for a response testing apparatus 404 for a conscious sedation system 400. The response testing apparatus 404 includes a request assembly 408 and a response assembly 410. The request assembly 408 communicates to a patient 406 a request generated by a controller 402 of the conscious sedation system 400 for a predetermined hand motion response from the patient 406. The response assembly 410 senses a hand motion response made by the patient 406 to the request and communicates the hand motion response to the controller 402 which analyzes at least the hand motion response to determine a level of sedation of the patient 406.

In one example of the third expression of the embodiment of FIG. 4-1, the response assembly 410 senses at least one of a translation and a rotation of the hand of the patient 406.

A first example of the response assembly 410 includes a motion detector (such as an accelerometer 420, 422 and 424) supportable by the hand of the patient 406 (such as by using a handpiece 416).

A second example of the response assembly 410, shown in FIG. 4-4, includes a telemetry tracking system 428 for tracking hand motion of the patient 406. In one construction, the telemetry tracking system 428 includes a transponder 430 attachable to the hand of the patient 406. In one variation, the transponder 430 is attachable to a finger of the hand wherein the patient has been told, in making the predetermined hand motion response, to move the hand without moving the finger relative to the palm of the hand. In this construction, the telemetry tracking system 428 additionally includes three receivers 432 wherein each receiver receives a signal from the transponder 430 as is understood by the artisan.

Figures 1, 2:
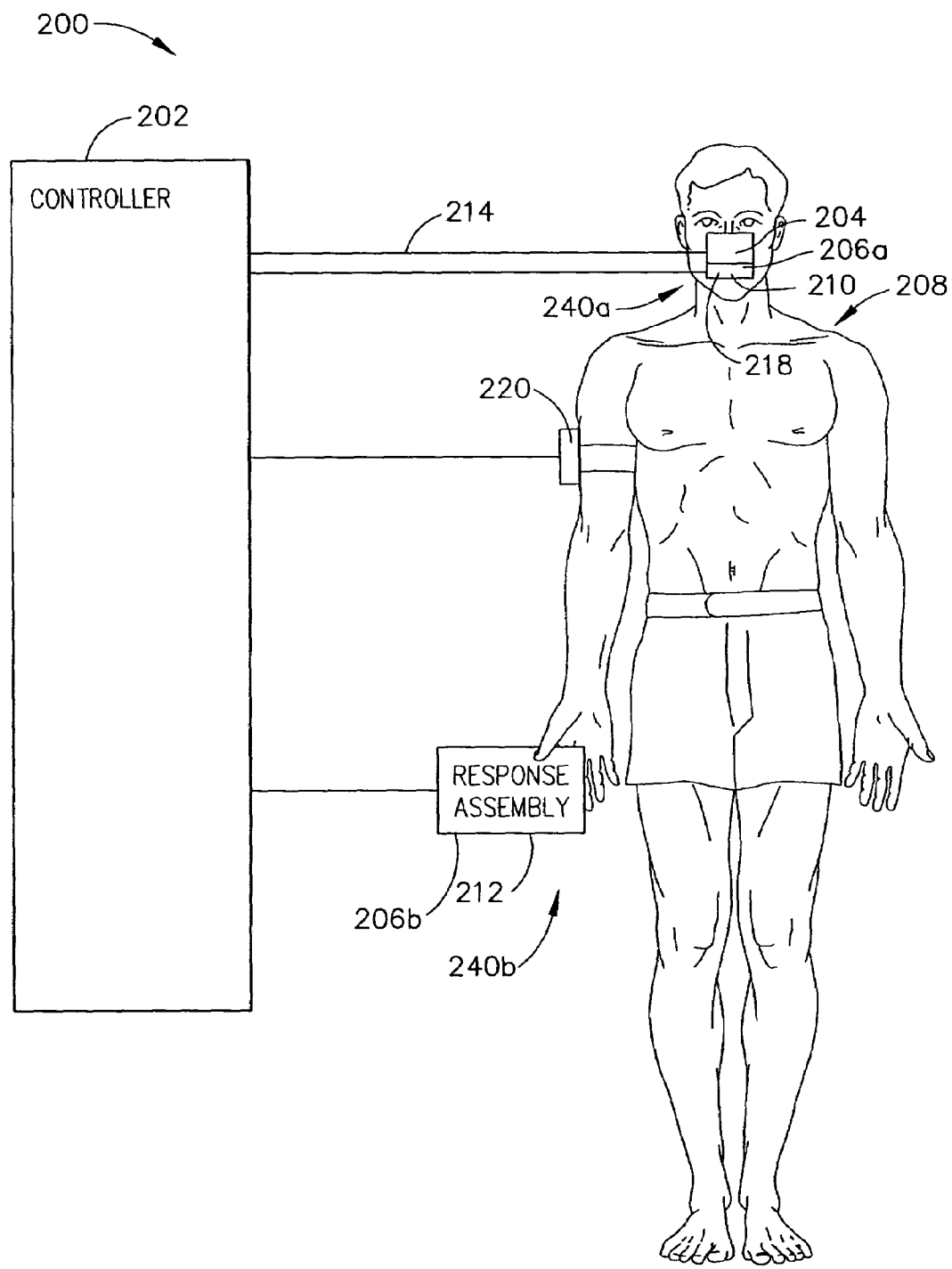
Figure 2:
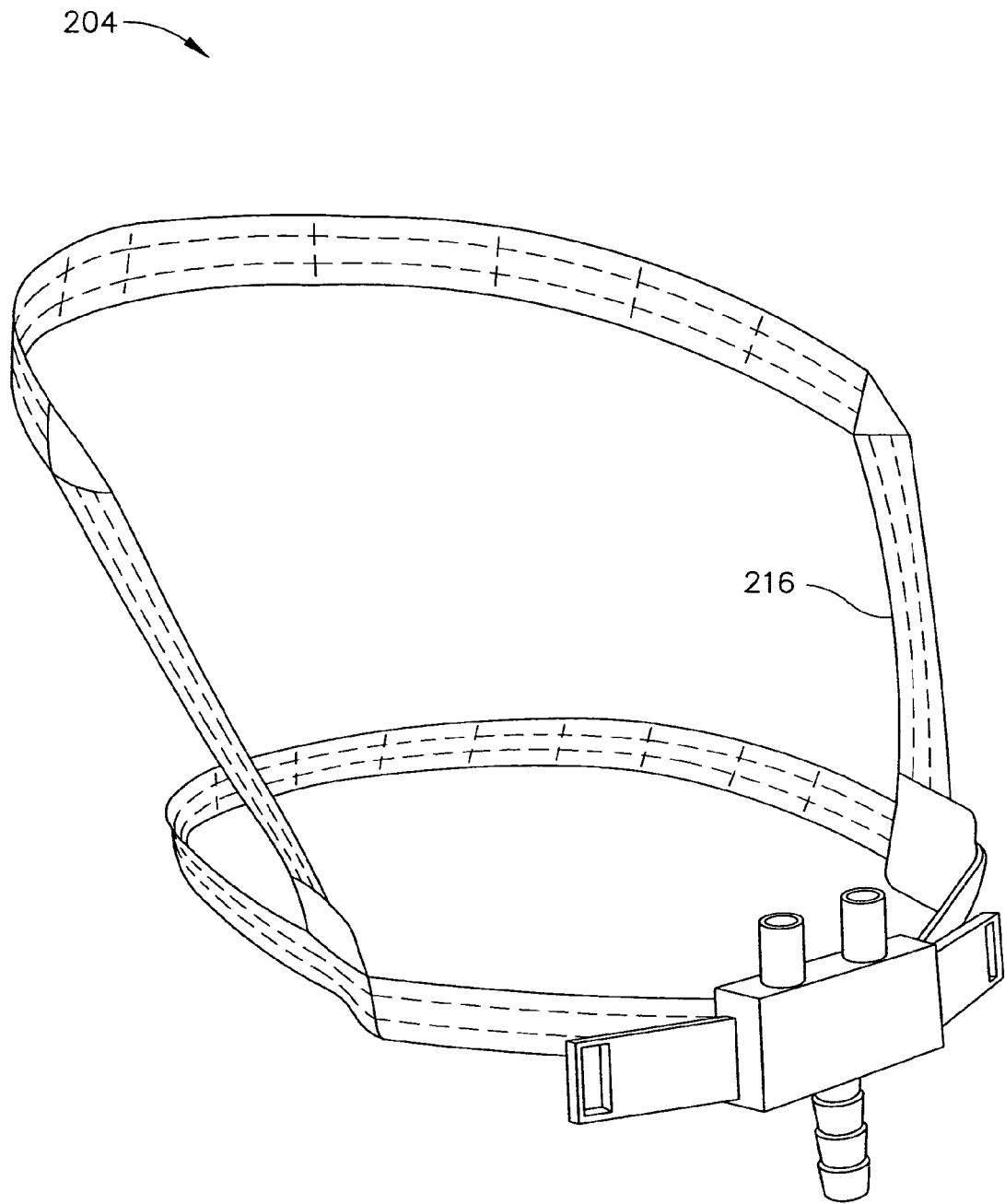
Figures 2, 3:
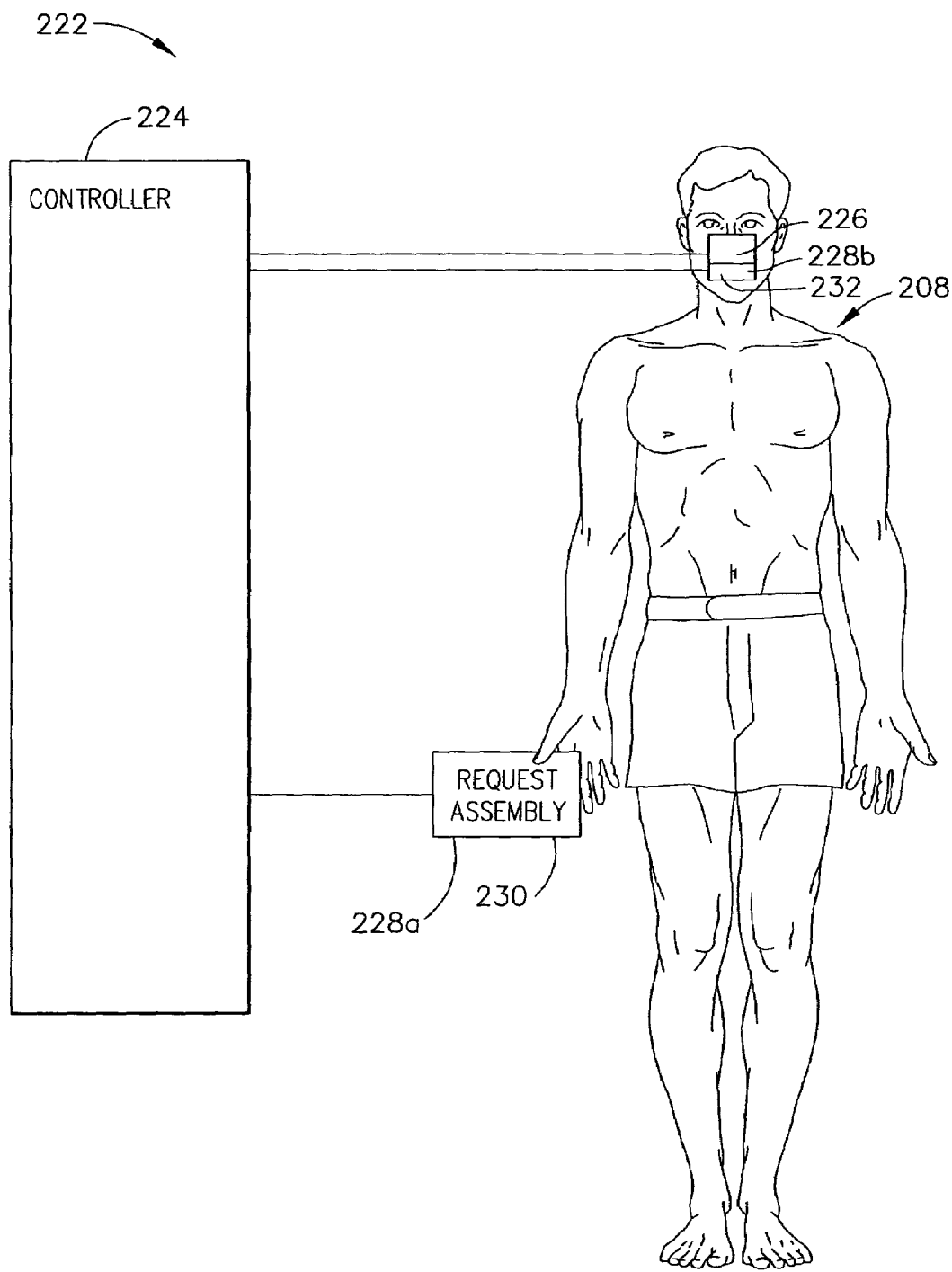
Figures 2, 3, 4:
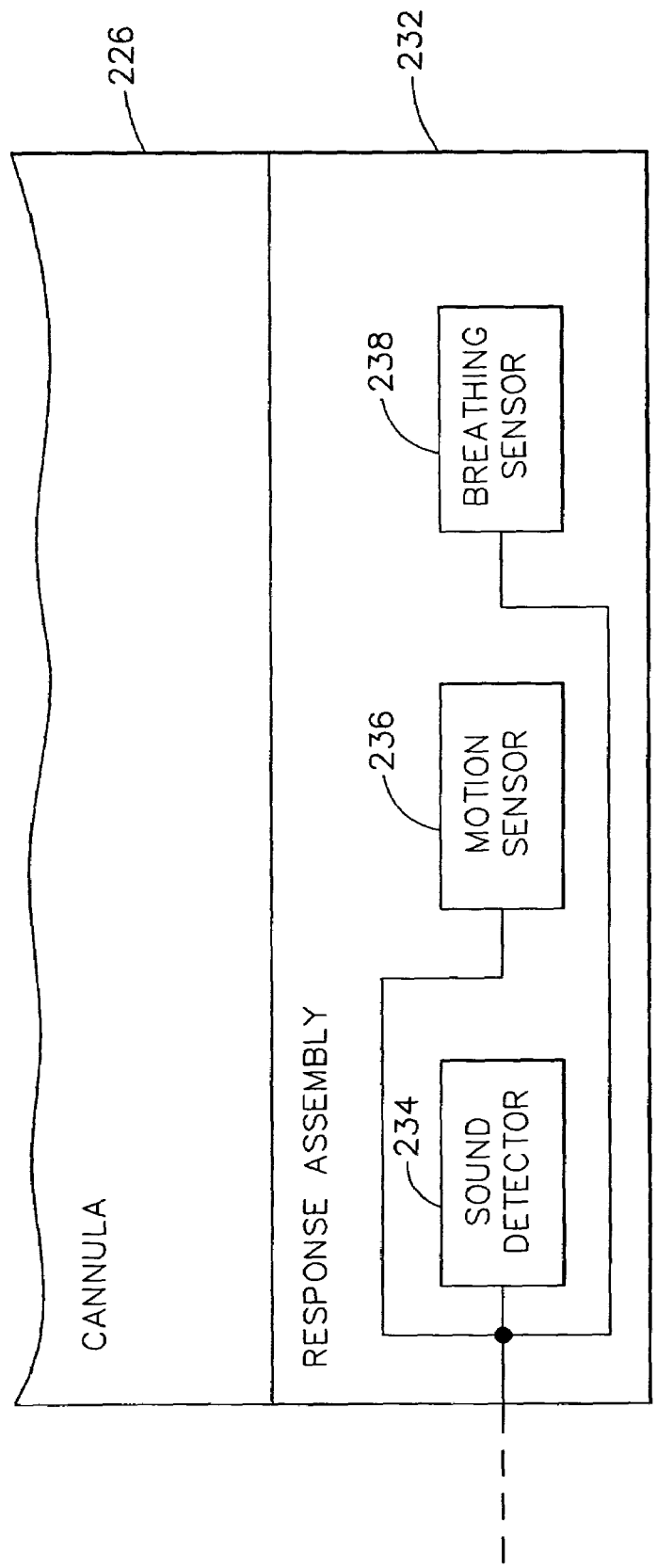
Figures 2, 3, 4, 5:
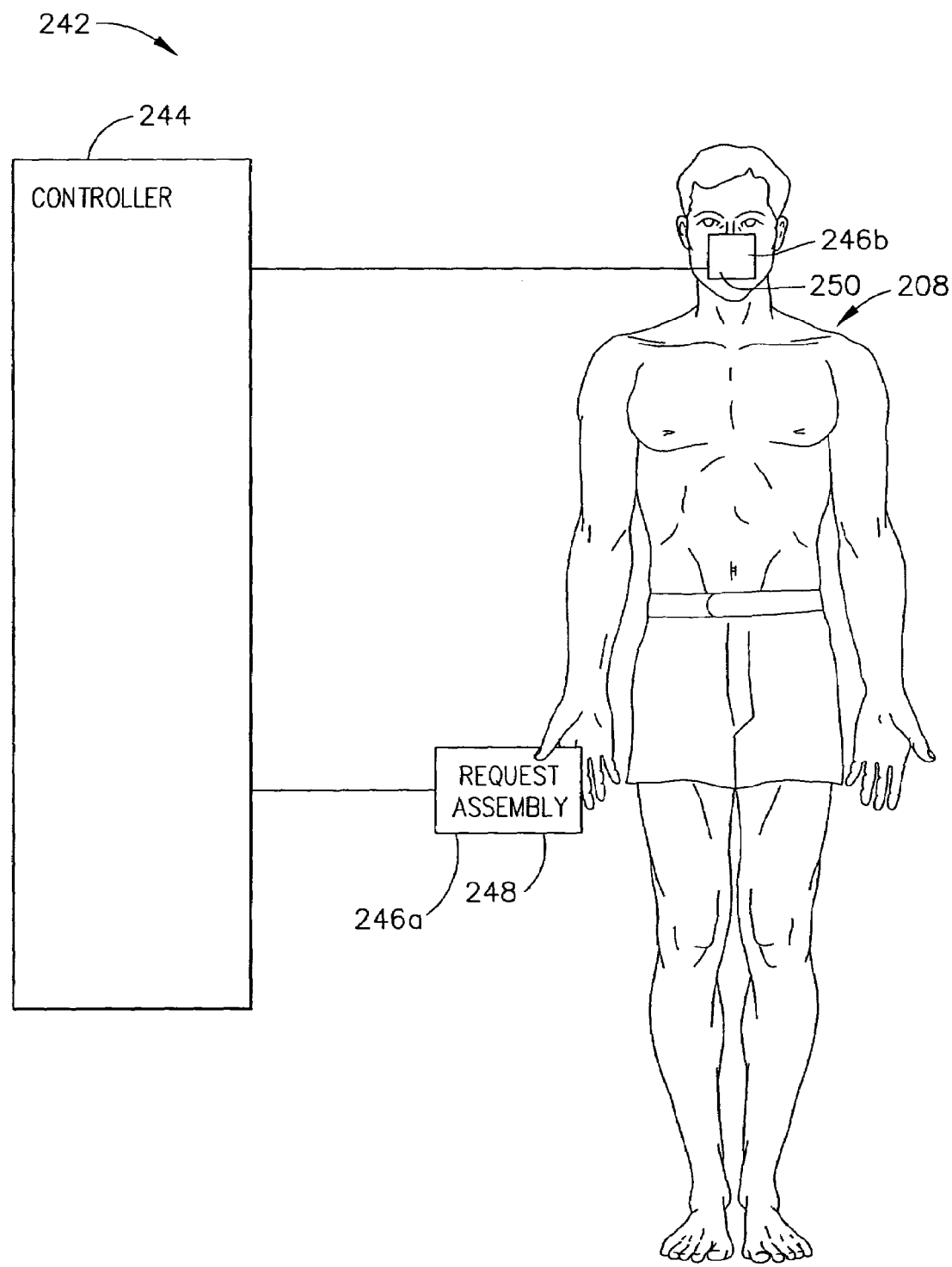
Figures 1, 3:
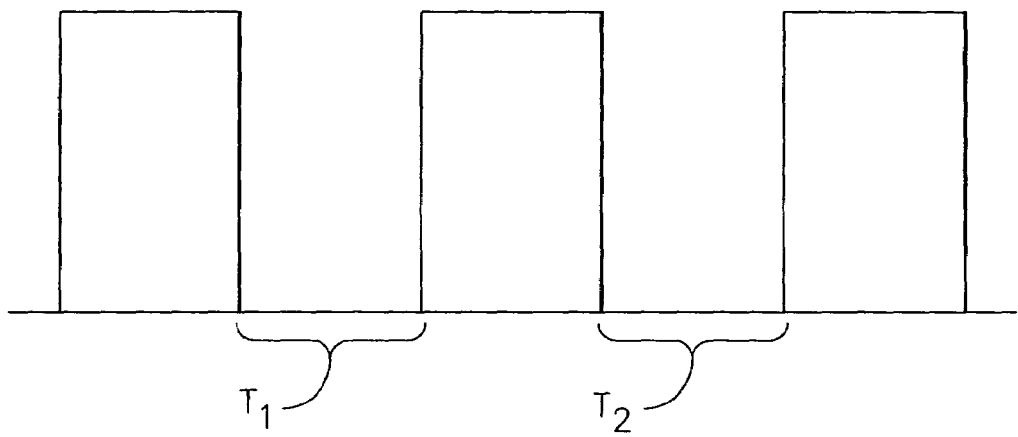
Figures 2, 3:
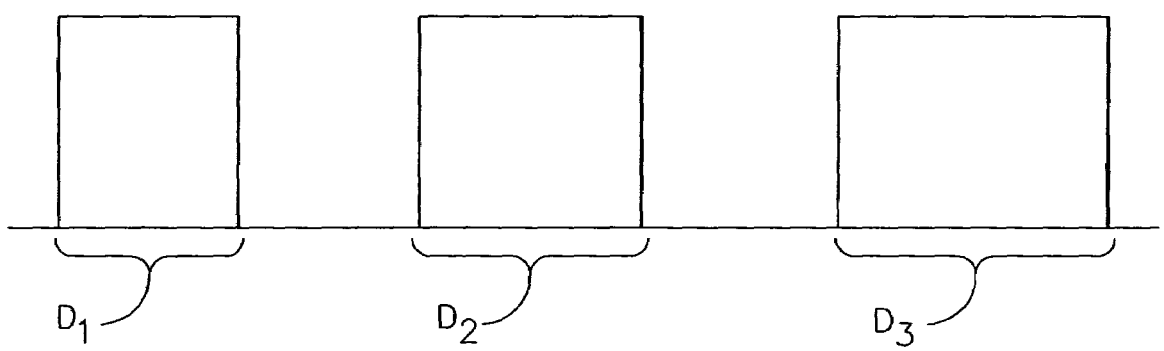
Figure 3:
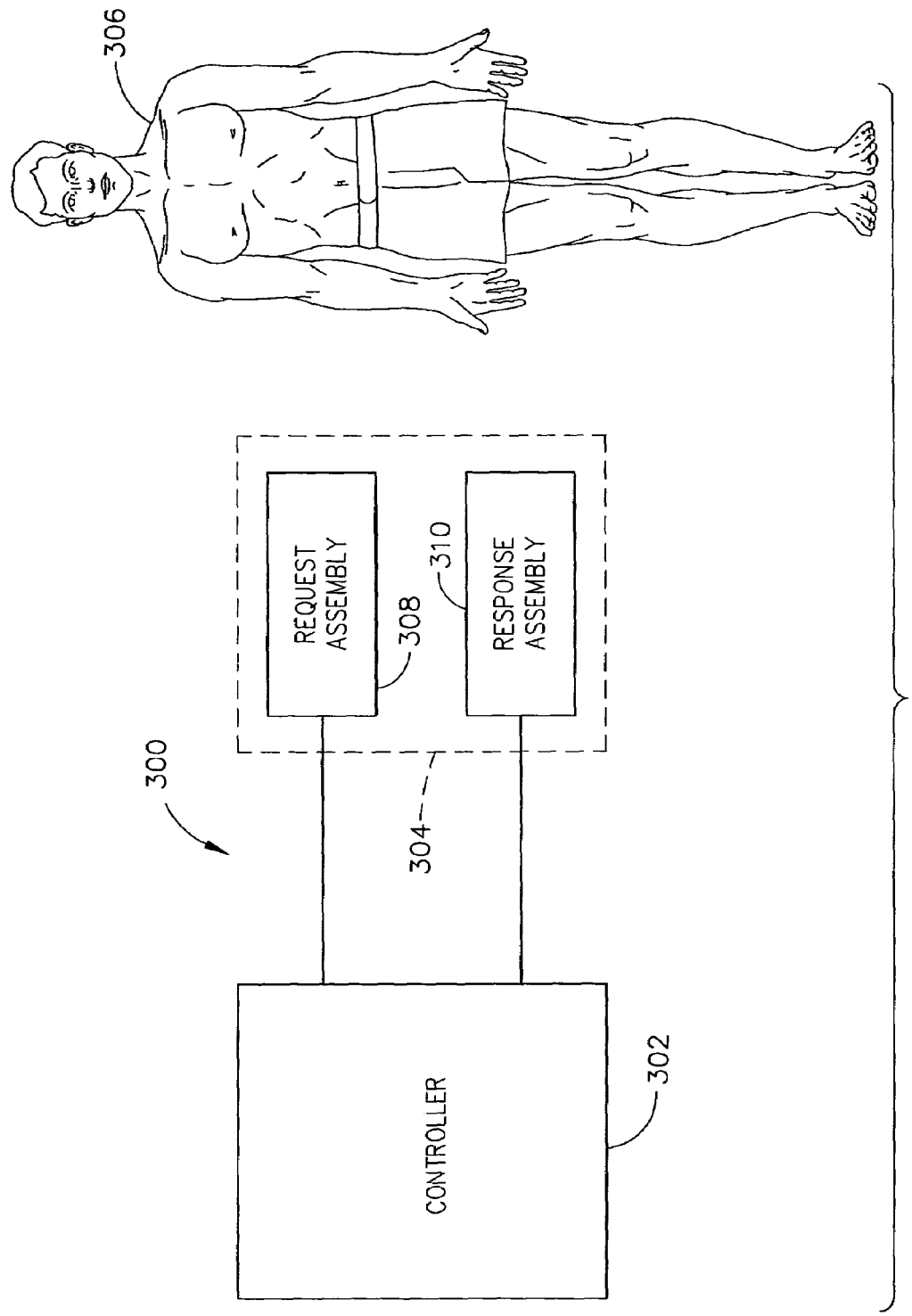
Figures 3, 4:
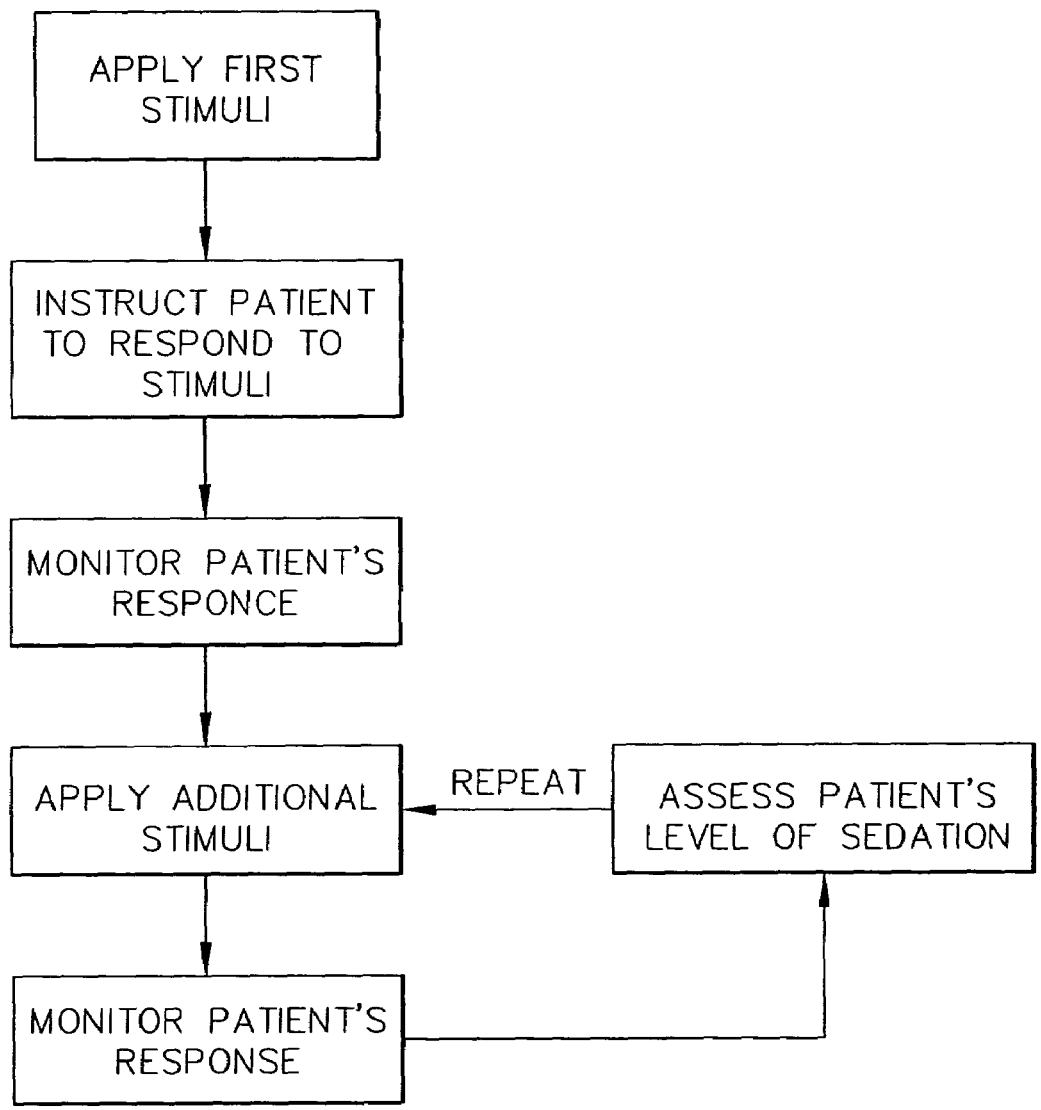
Figures 1, 4:
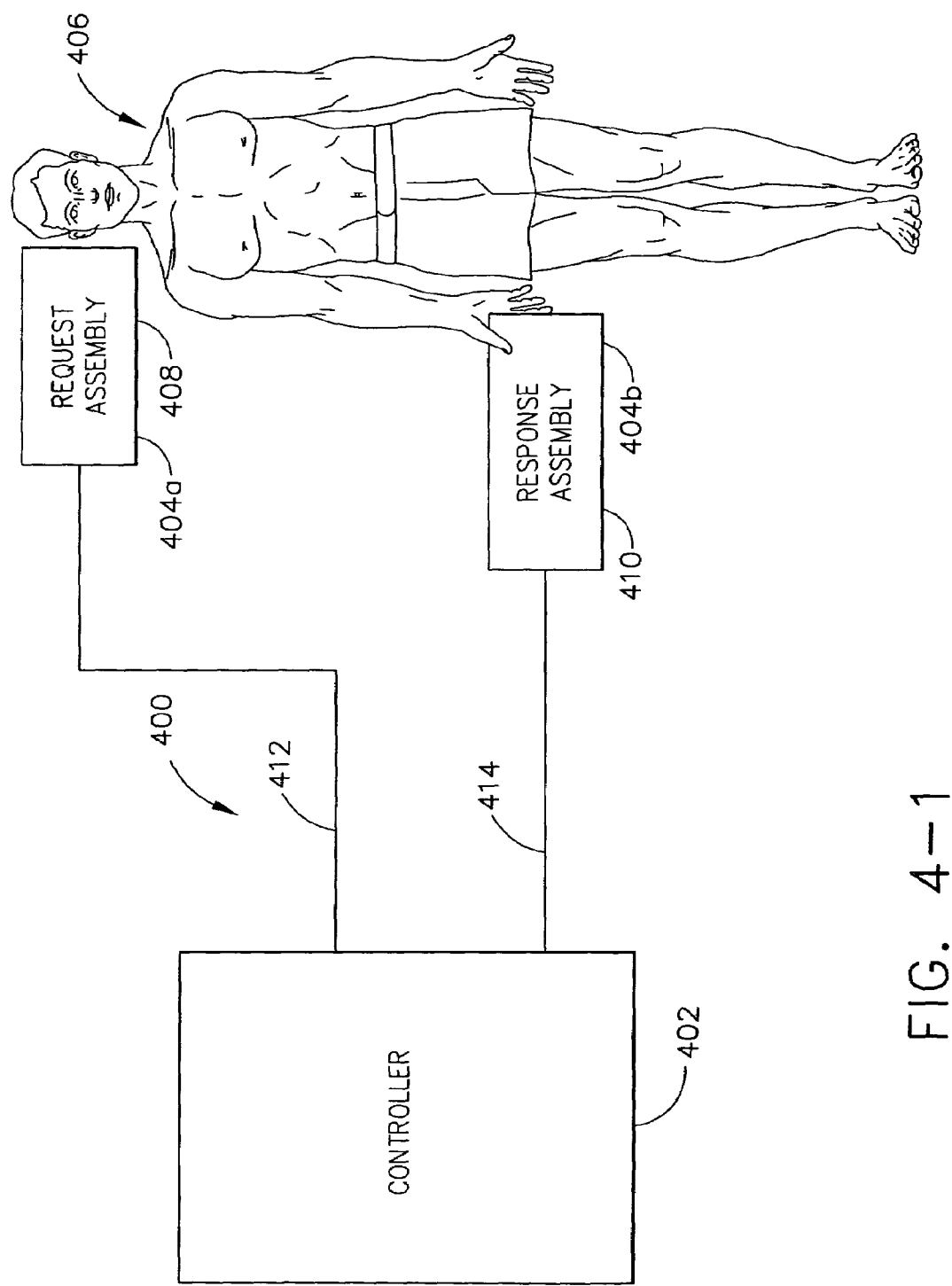
Figures 3, 4:
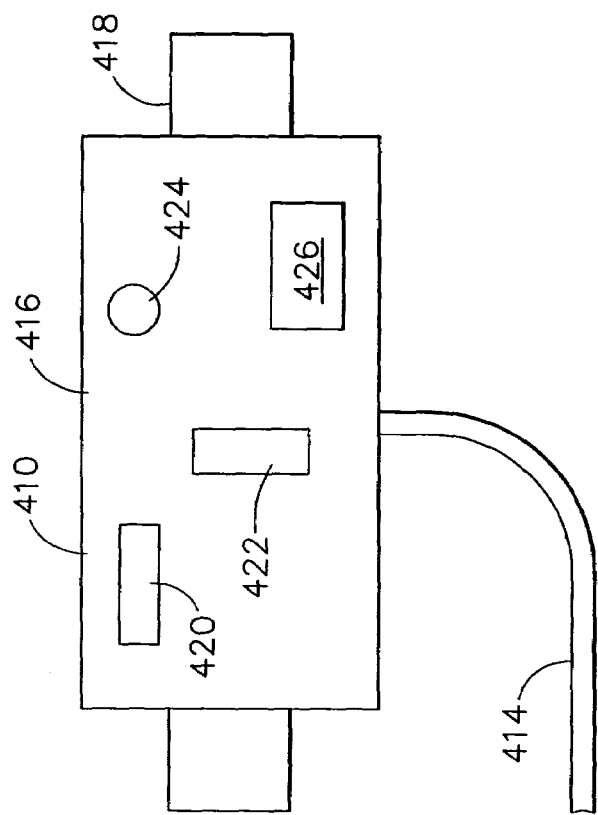
Figures 2, 4:
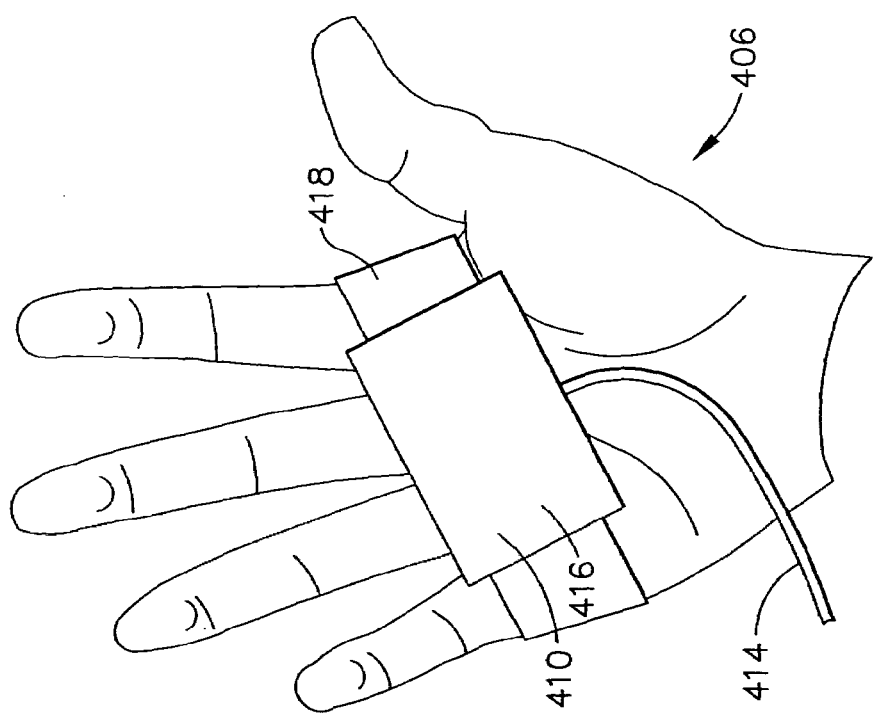
Figures 4, 5:
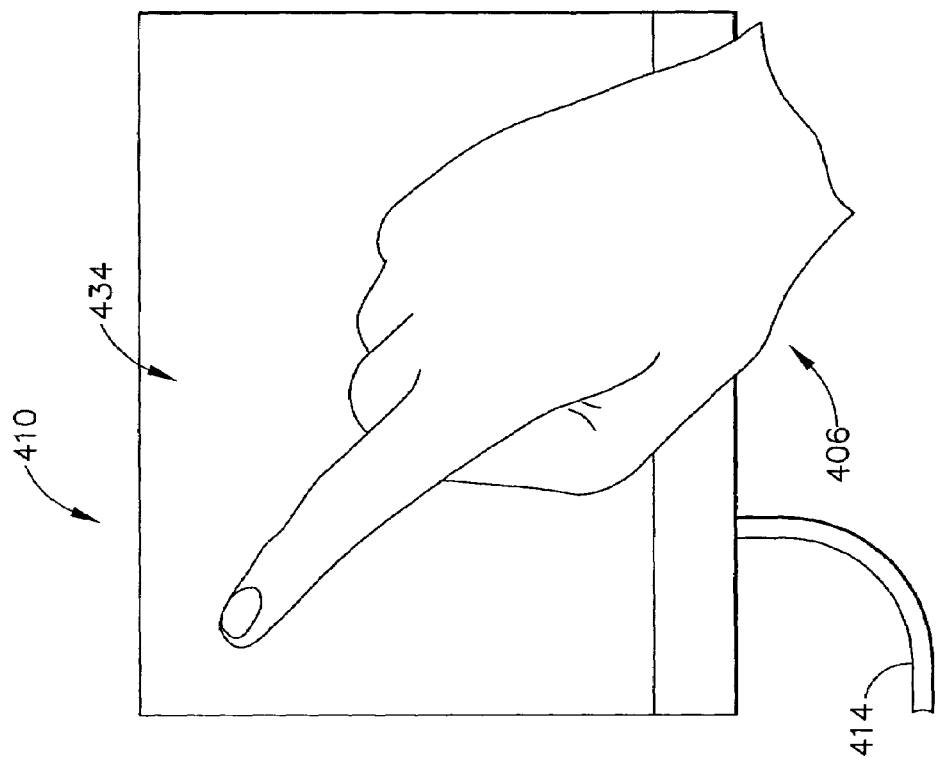
Figure 4:
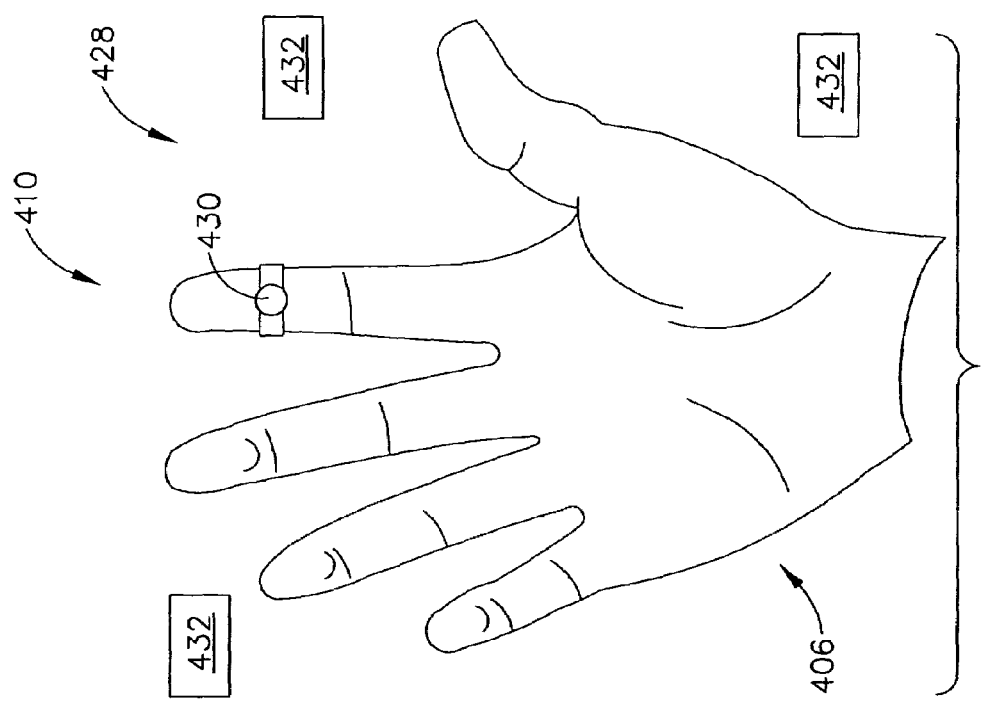

A third example of the response assembly 410, shown in FIG. 4-5, includes a touch pad 434 disposable proximate the hand of the patient 406. In one variation, the touch pad 434 is disposed on the hospital bed occupied by the patient 406. Other locations for the touch pad 434 are left to the artisan. In one construction, the touch pad converts hand contact of the patient 406 to position information of the touched site on the touch pad 434 and communicates such positional information to the controller 402.

Advantages and benefits of one or more of the expressions of the embodiment and examples, etc. of FIGS. 4-1 to 4-5 include a finer determination of the level of sedation of a patient undergoing a medical procedure involving conscious sedation. Also, hand motion responses are easier for a patient undergoing conscious sedation to make than activating a switch on a handpiece. It is noted that hand motion responses do not require grip strength and are easier for patients to make whose grip strength is impaired. Eliminating switches provides for greater reliability as switches need to be sealed against moisture and debris.

Conscious Sedation Involving Dynamics of a Hand Grip Patient Response

A fifth aspect of the invention relates to conscious sedation and involves the dynamics of a hand grip patient response. Referring now to the drawings, FIG. 5-1 illustrates a first embodiment of the fifth aspect of the invention. A first expression of the first embodiment is for a conscious sedation system 500 including a controller 502 and a response testing apparatus 504 (wherein parts 504a and 504b are parts of the response testing apparatus 504). The controller 502 generates a request for a predetermined hand grip response from a patient 506 and analyses at least a dynamic variable of a hand grip response made by the patient 506 to the request to determine a level of sedation of the patient. The response testing apparatus 504 includes a request assembly 508 and a response assembly 510. The request assembly 508 communicates to the patient 506 the request generated by the controller 502. The response assembly 510 senses the dynamic variable of the hand grip response and communicates the dynamic variable to the controller 502.

By "hand grip response" is meant the response of a patient using a hand, or one or more fingers and/or a thumb thereof, to squeeze or exert pressure. Examples of a hand grip response include, without limitation, a patient using a hand to squeeze or try to squeeze a handpiece and a patient using a finger to depress a plunger. By "sensing a dynamic variable" is meant sensing the varying value of a dynamic variable. A "dynamic variable" includes, without limitation, applied force (or pressure), the time rate of the applied force (or pressure), the distance moved, the velocity of movement, and the acceleration of movement. A "dynamic variable" does not include a switch which is either activated or not activated and does not include the time between a request and a response or the time between two responses.

In one implementation of the first expression of the embodiment of FIG. 5-1, certain patient vital signs such as blood pressure, blood oxygen saturation (oximetry) and inhalation and exhalation carbon dioxide levels (capnometry) are electronically monitored and are also analyzed by the controller 502, in addition to the response from the response assembly 510, to determine a level of sedation of the patient. The term "controller", without limitation, includes one controller and includes two or more spaced-apart subcontrollers, etc. Examples of request assemblies 508 in FIG. 5-1 include a handpiece having a vibrator and secured to the hand of the patient 506 and an earphone speaker disposed in the ear of the patient 506. Other request assemblies include vibrators supported by a blood pressure cuff, supported by a pulse oximeter disposable on a finger or ear lobe of the patient, or supported by another medical device. Additional request assemblies include vibrators placed upon the face, head, neck, or upper spine of the patient. In one design, a cable 512 operatively connects the controller 502 to the request assembly 508, and a cable 514 operatively connects the response assembly 510 to the controller 502.

In one example of the first expression of the embodiment of FIG. 5-1, a user and/or the controller 502 determines a delivery schedule (including any interruption of delivery) of a conscious-sedation drug to the patient 506 based at least in part on the determined level of sedation of the patient 506. The drug delivery apparatus has been omitted from FIG. 5-1 for clarity. A conscious sedation drug is a drug or drug combination which, in an efficacious amount, is capable of sedating the patient 506 during a medical procedure (such as a colonoscopy) while keeping the patient 506 conscious. Conscious sedation drugs, such as Propofol, are well known in the medical art. In one alternative, a user such as a doctor, instead of the controller 502, determines a delivery schedule of the conscious-sedation drug to the patient 506 based at least in part on the determined level of sedation of the patient 506.

In one design of the first expression of the embodiment of FIG. 5-1, the response assembly 510 senses a nerve signal sent by the brain of the patient 506 to activate a muscle which is used by the patient 506 to make a hand grip response. In one variation, one or more electrodes are applied to the hand, wrist, etc. and are monitored for EMG (electromyography) or other neural activity, wherein, in one embodiment, the electrodes are part of a handpiece. In one modification, the EMG activity/intensity, when the patient squeezes a handpiece, is considered by the controller 502 to be proportional to the level of sedation of the patient (with other inputs used by the controller in determining the level of sedation being equal), as can be appreciated by those skilled in the art. It is noted that the electrode can detect a weak attempt of the patient to make a hand grip response, including a patient response with no detectable movement but detectable muscle fiber firing.

In another design of the first expression of the embodiment of FIG. 5-1, the response assembly 510 includes a handpiece 516, as shown in FIG. 5-2. The handpiece 516 is disposable in a hand of the patient 506. The handpiece 516 senses the dynamic variable of the hand grip response and communicates the dynamic variable to the controller 502. In one application, the handpiece 516 is attachable to the hand of the patient 506, such as through use of a band 518.

In one arrangement, the handpiece 516 senses the force of the hand grip response. In one construction, the handpiece 516 includes a force sensor 520 as shown in FIG. 5-3, wherein the controller 502 at least analyzes at least one of the amount of force of the hand grip response and the time variation of the amount of force of the hand grip response to determine the level of sedation of the patient 506. Force sensors 520 include, without limitation, a strain gauge, a variable force resistor, and a piezo device as can be appreciated by the artisan. Force sensors can be placed on or in the handpiece to react to a squeeze of the hand and can be placed in the handpiece to react to the finger or thumb displacement of a plunger.

In the same or a different construction, the handpiece 516 includes a displacer 522, and the controller 502 at least analyzes at least one of the distance that the displacer 522 is moved, the velocity of the displacer 522, and the acceleration of the displacer 522 to determine the level of sedation of the patient 506. In one variation, the controller 502 analyzes at least two of the distance, the velocity, and the acceleration of the displacer 522 to determine the level of sedation of the patient 506. In one modification, the controller 502 analyzes at least the distance, the velocity, and the acceleration of the displacer 522 to determine the level of sedation of the patient 506. In one application, the displacer 522 is a finger or thumb displaced plunger 524 wherein the plunger is spring loaded, otherwise equipped, to return to its original non-depressed position when the patient is not displacing the plunger.

In one enablement of the first expression of the embodiment of FIG. 5-1, the controller 502 generates a feedback signal which is communicated (in one example by a "clicker" 526 (such as, for example, a solenoid or displaceable diaphragm) in the handpiece 516) to the patient 506 when the hand grip response from the patient 506 meets a predetermined criteria.

In the same or a different enablement, the controller 502 changes the predetermined criteria between two requests and at least analyzes the hand grip responses from the two requests to determine the level of sedation of the patient 506. For example, a patient 506 who passes a two-millimeter per second velocity criteria for a finger displaced plunger 524 but fails a four-millimeter per second velocity criteria is considered by the controller 502 (with other inputs used by the controller for determining the level of sedation being equal) to be at a deeper level of sedation than a patient who passes both criteria.

In the same or a different enablement, the handpiece 516 is adjustable (or automatically adapts) in compliance and/or size to respond to one of a lower hand grip force and/or size and a higher hand grip force and/or size. This enables the same handpiece 516 to be used by a patient having a weak grip and by a patient having a strong grip. In one variation, a motor (not shown) having an adjustable biasing voltage resists the motion of the plunger 524, wherein the biasing voltage is set low to respond to a patient with a weaker grip (e.g., one to five pounds of hand grip force) and is set high to respond to a patient with a stronger grip (e.g., twenty to thirty pounds of hand grip force). In one modification, a high-to-low resistance adjustment is made to take place when the patient 506 reaches an acceptable hand grip response so that the following "collapse" of the handpiece 516 acts as a feedback to the patient 506 indicating a successful hand grip response.

A second expression of the embodiment of FIG. 5-1 is for a response testing apparatus 504 for a conscious sedation system 500. The response testing apparatus 504 includes a request assembly 508 and a response assembly 510. The request assembly 508 communicates to a patient 506 a request generated by a controller 502 of the conscious sedation system 500 for a predetermined hand grip response from the patient 506. The response assembly 510 senses a dynamic variable of a hand grip response made by the patient 506 to the request and communicates the dynamic variable to the controller 502 which analyzes at least the dynamic variable to determine a level of sedation of the patient 506.

In one example of the second expression, the dynamic variable is chosen from the group consisting of the amount of force of the hand grip response, the time variation of the amount of force of the time grip response, the distance of the hand grip response, the velocity of the hand grip response, and the acceleration of the hand grip response. In one variation, the response assembly 510 senses the amount of force of the hand grip response, and the controller 502 calculates the time variation of the amount of force of the time grip response. In the same or a different variation, the response assembly 510 senses the distance of the hand grip response, and the controller 502 calculates the velocity (i.e., the time variation of the distance) and/or the acceleration (i.e., the time variation of the velocity).

In the same or a different example, a user and/or the controller 502 determines a delivery schedule of a conscious-sedation drug to the patient 506 based at least in part on the determined level of sedation of the patient.

A third expression of the embodiment of FIG. 5-1 is for a response assembly 510 for a response testing apparatus 504 for a conscious sedation system 500, wherein the response testing apparatus 504 includes a request assembly 508 which communicates to a patient 506 a request generated by a controller 502 of the conscious sedation system 500 for a predetermined hand grip response from the patient 506. The response assembly 510 includes a handpiece 516 which senses a dynamic variable of a hand grip response made by the patient 506 to the request and which communicates the dynamic variable to the controller 502 which analyzes at least the dynamic variable to determine a level of sedation of the patient 506.

In one example of the third expression of the embodiment of FIG. 5-1, the response assembly 510 includes a resistance handpiece 528 (seen in FIG. 5-4) which includes an electrical resistance sensor 530 having two electrodes 532 and 534 each contactable with the skin of the patient 506 (or a conductive glove worn by the patient) when the patient grips the resistance handpiece 528, wherein the skin (or glove) exerts a variable pressure on the two electrodes 532 and 534 during the hand grip response. For purposes of describing the invention, the term "resistance" includes "impedance". It is noted that the "electrical circuit" whose resistance is being measured is the skin path (i.e., the galvanic skin response) of the patient 506 between the two electrodes 532 and 534. As the patient 506 grips the resistance handpiece 528 with a stronger force, more of the skin contacts the two electrodes 532 and 534 which changes the electrical resistance as measured by the electrical resistance sensor 530. In one variation, at least one of the two electrodes 532 and 534 has a surface roughness between and including 10,000 and 50,000 micro-inches.

In another example of the third expression of the embodiment of FIG. 5-1, the response assembly 510 includes a capacitance handpiece 536 (seen in FIG. 5-5) which includes an electrical capacitance sensor 538 and two conductors 540 and 542, wherein the hand grip response causes the distance between the two conductors 540 and 542 to vary. In a further example, the handpiece has a proximity sensor which detects the distance between two elements which changes as the handpiece is squeezed, and wherein the hand grip response causes the distance between the two elements to vary.

In an additional example of the third expression of the embodiment of FIG. 5-1, the response assembly 510 includes an air-bladder handpiece 544 (seen in FIG. 5-6) which includes a compliant air bladder 546, wherein the controller 502 analyzes at least the air pressure within the air bladder 546 to determine the level of sedation of the patient 506. In one variation, the air-bladder handpiece 544 includes a pressure sensor 548 which is disposed within the air bladder 546 and which sends a signal to the controller 502 corresponding to the air pressure within the air bladder 546. In an extension of the air-bladder concept, not shown, the air-pressure-movable protrusion of a thin area of the air bladder is used to activate a switch to signal the controller that a hand grip response has been made by the patient.

Figures 1, 5:
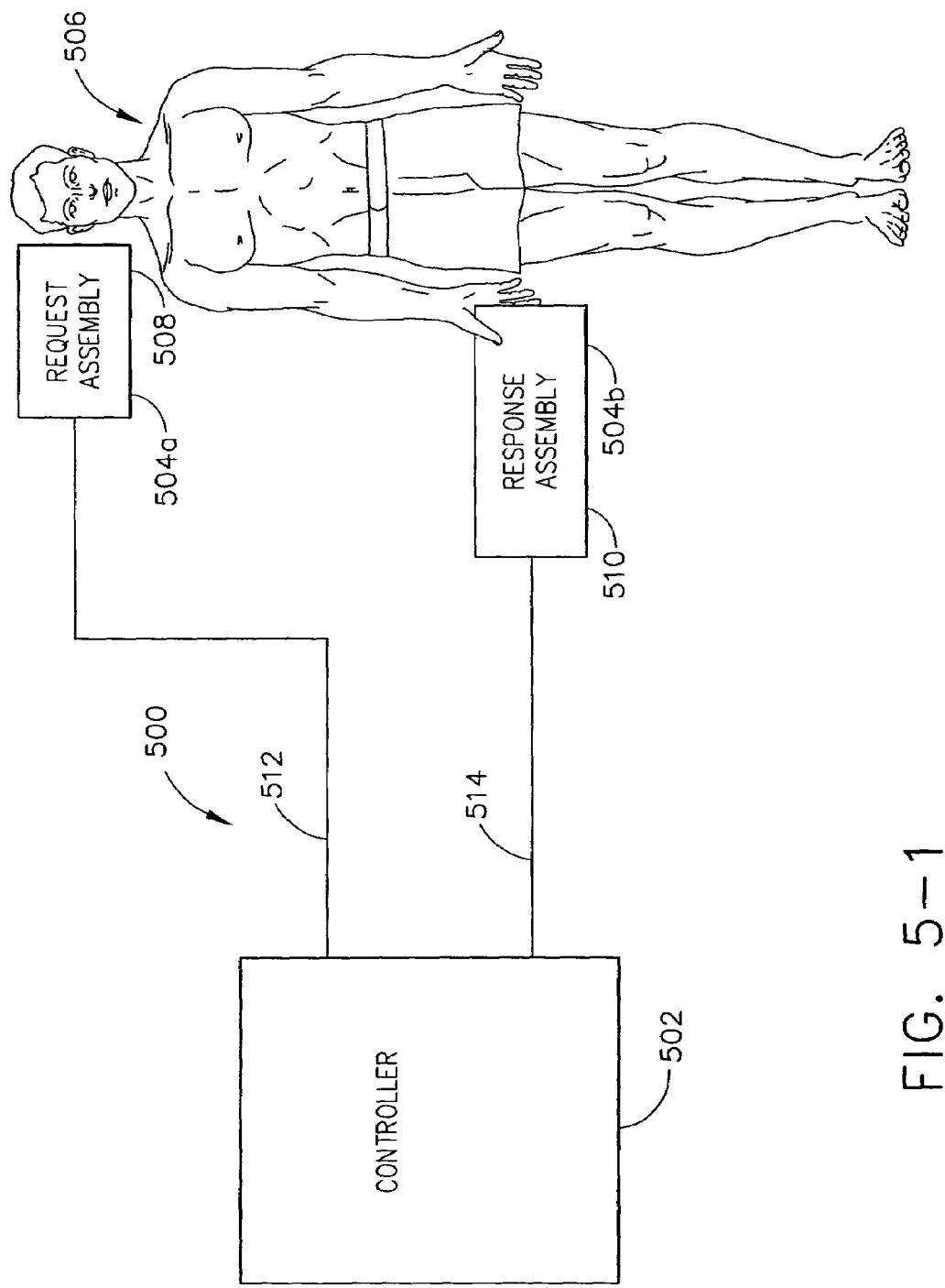
Figures 3, 5:
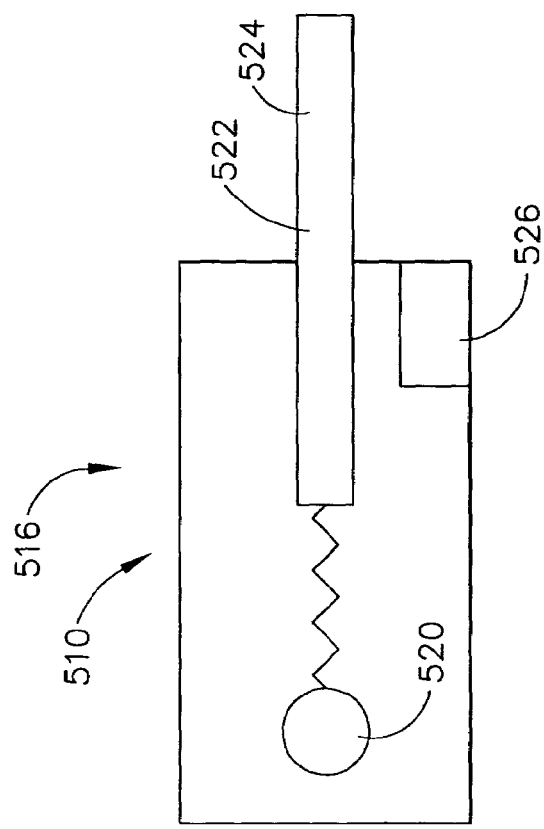
Figures 2, 5:
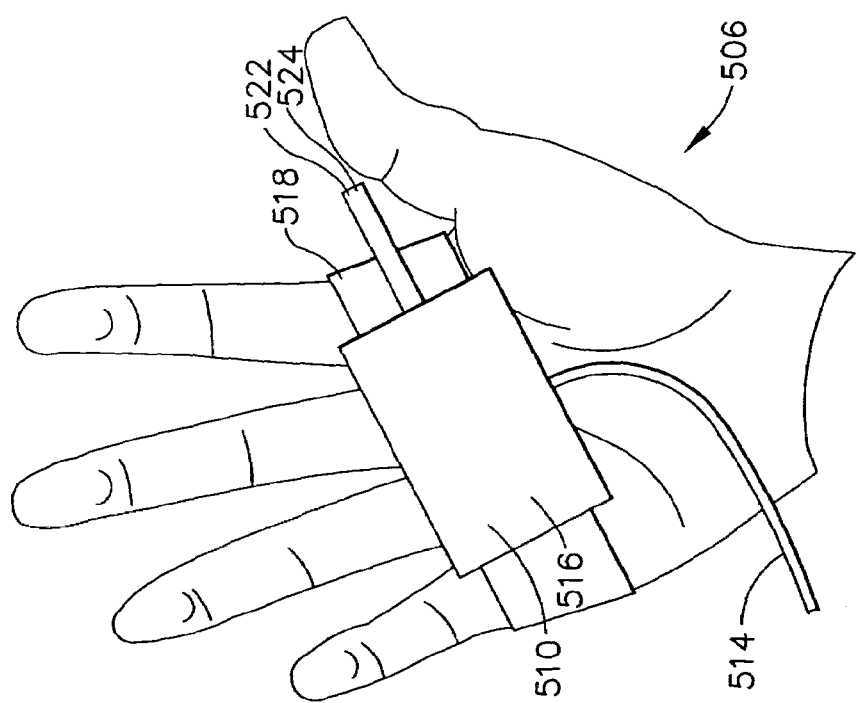
Figures 4, 5:
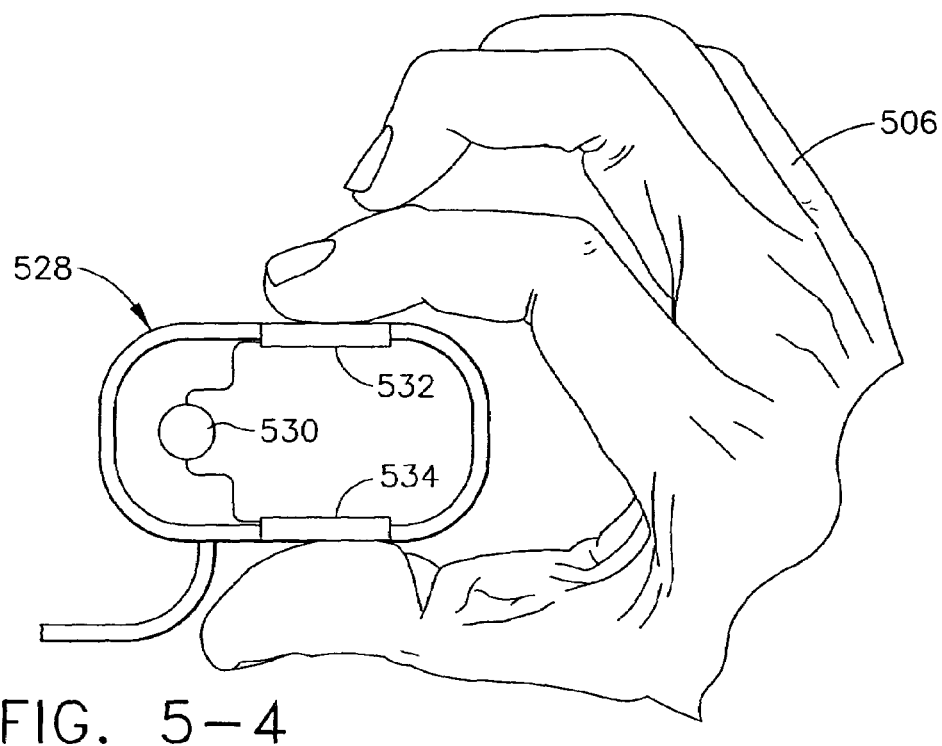
Figure 5:
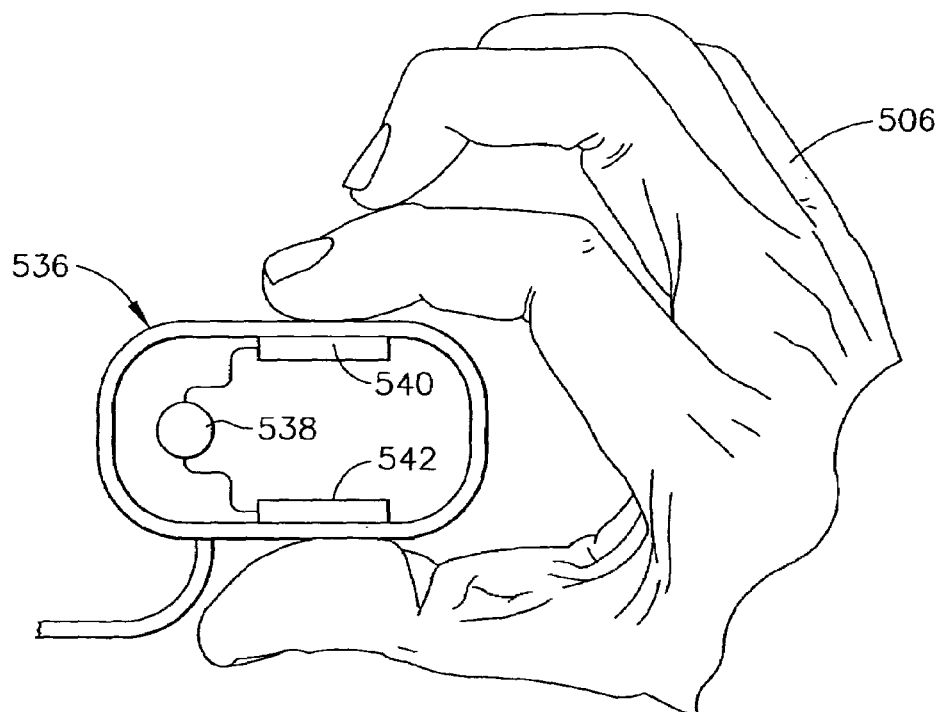
Figures 5, 6:
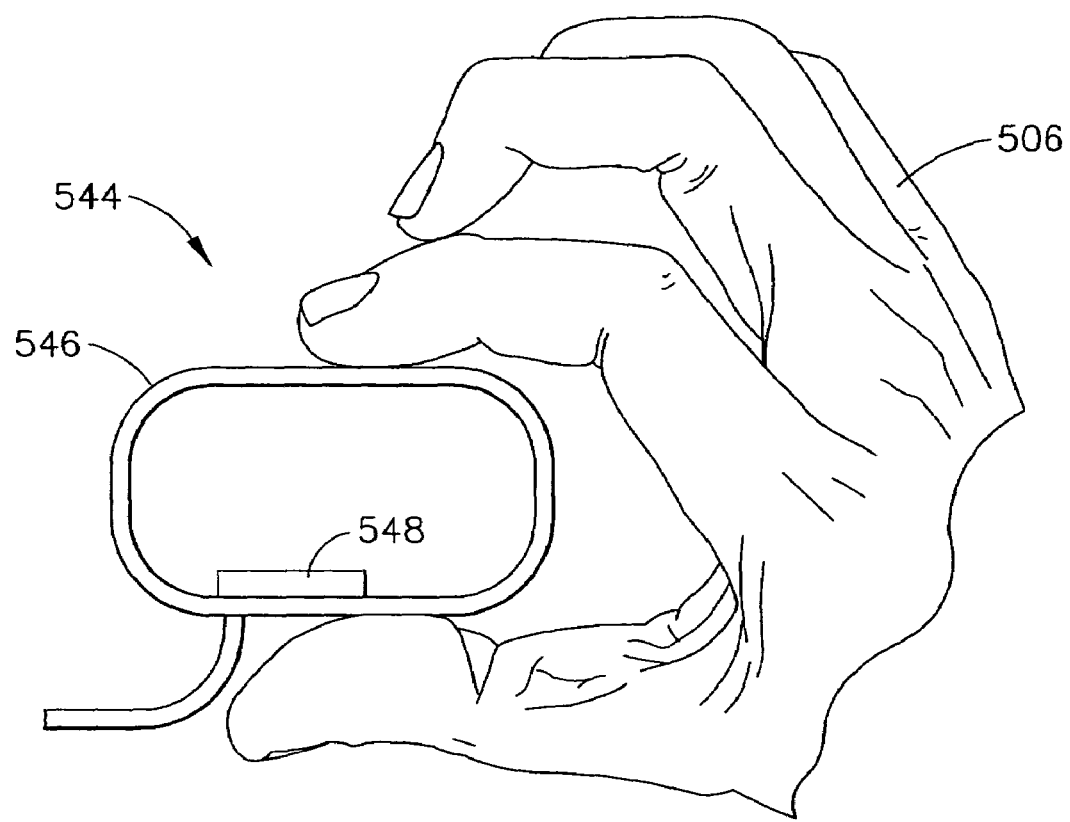
Figures 1, 6:
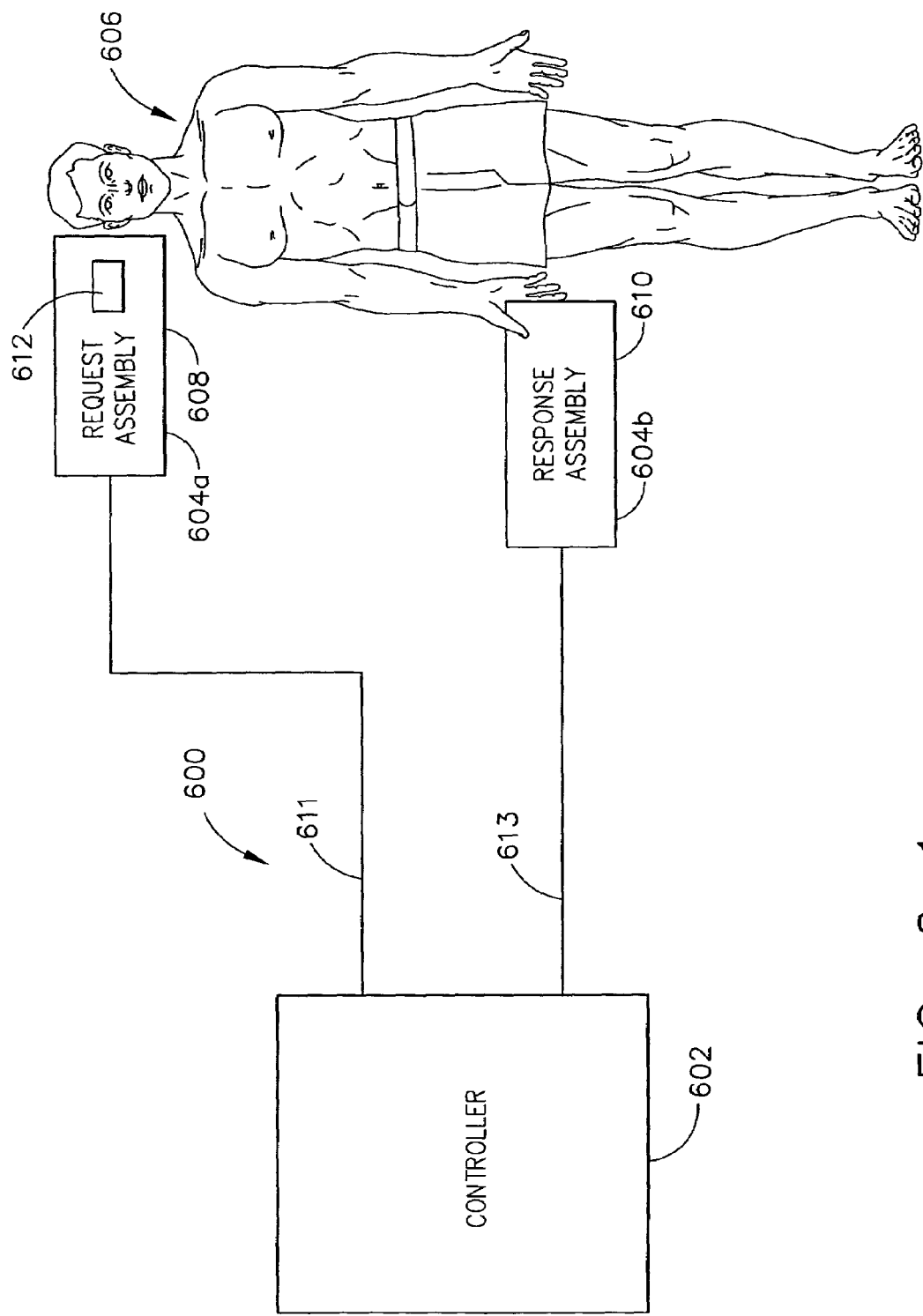
Figures 2, 6:
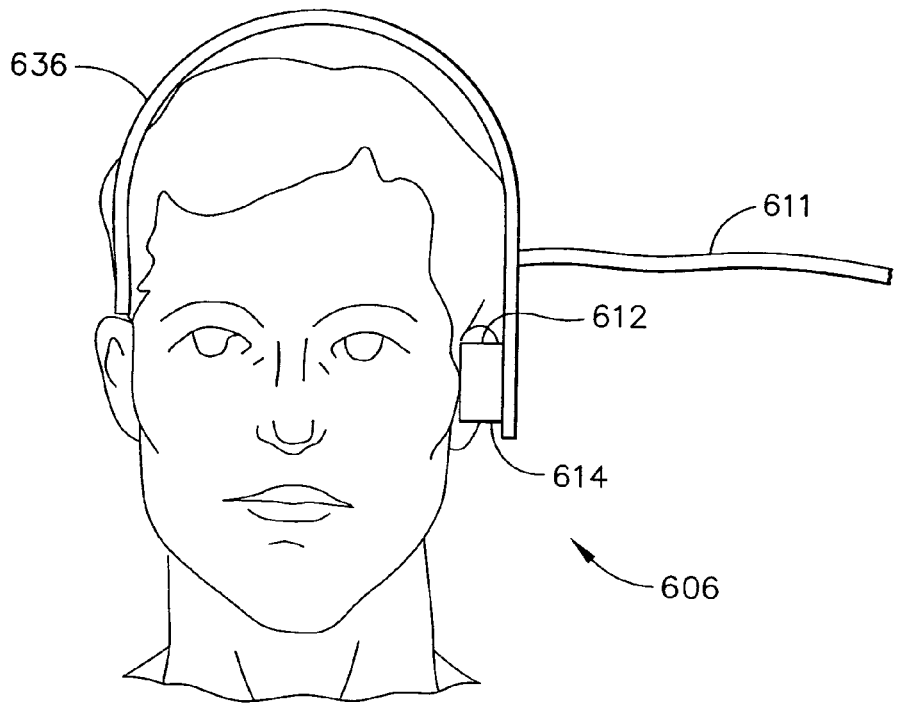
Figures 3, 6:
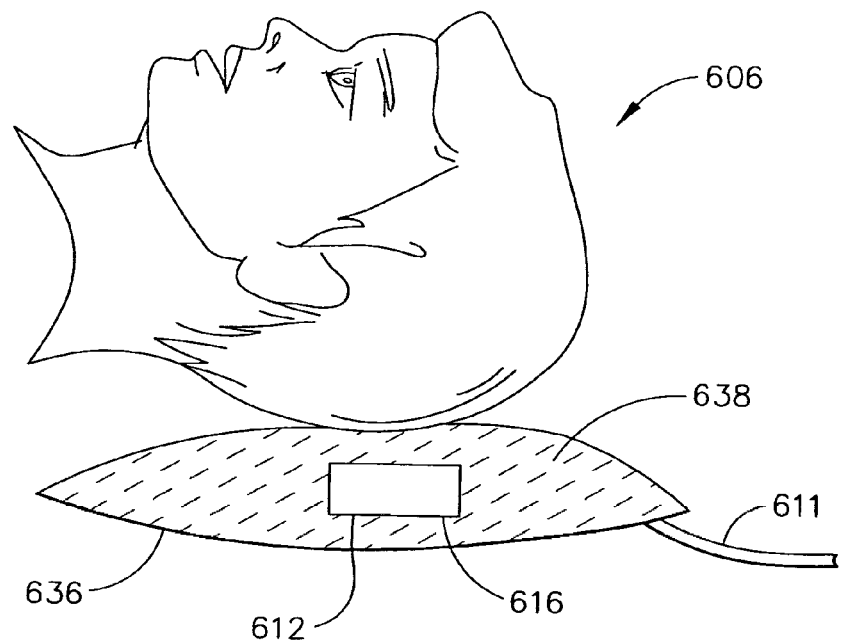
Figures 4, 6:
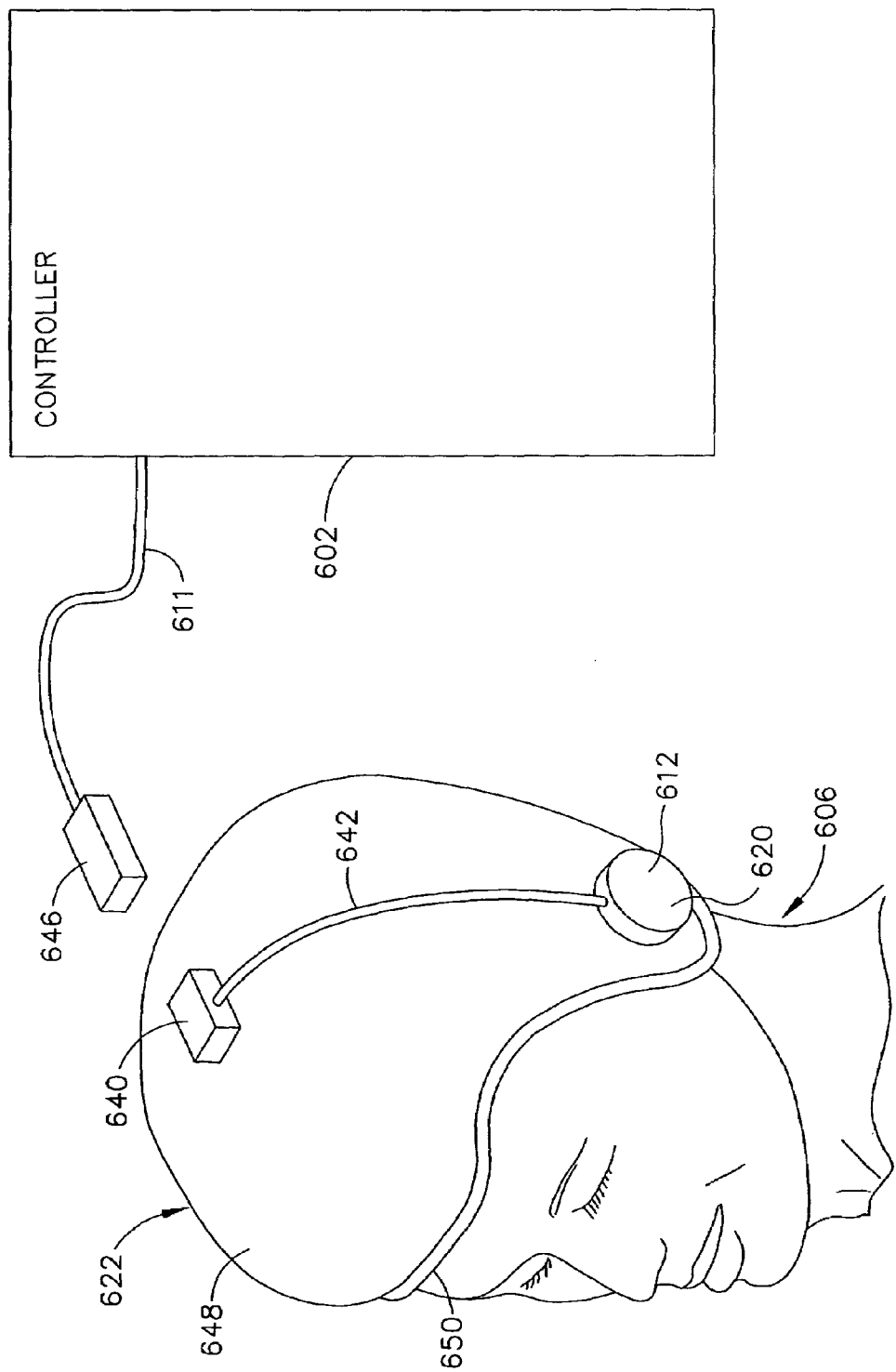
Figures 5, 6:
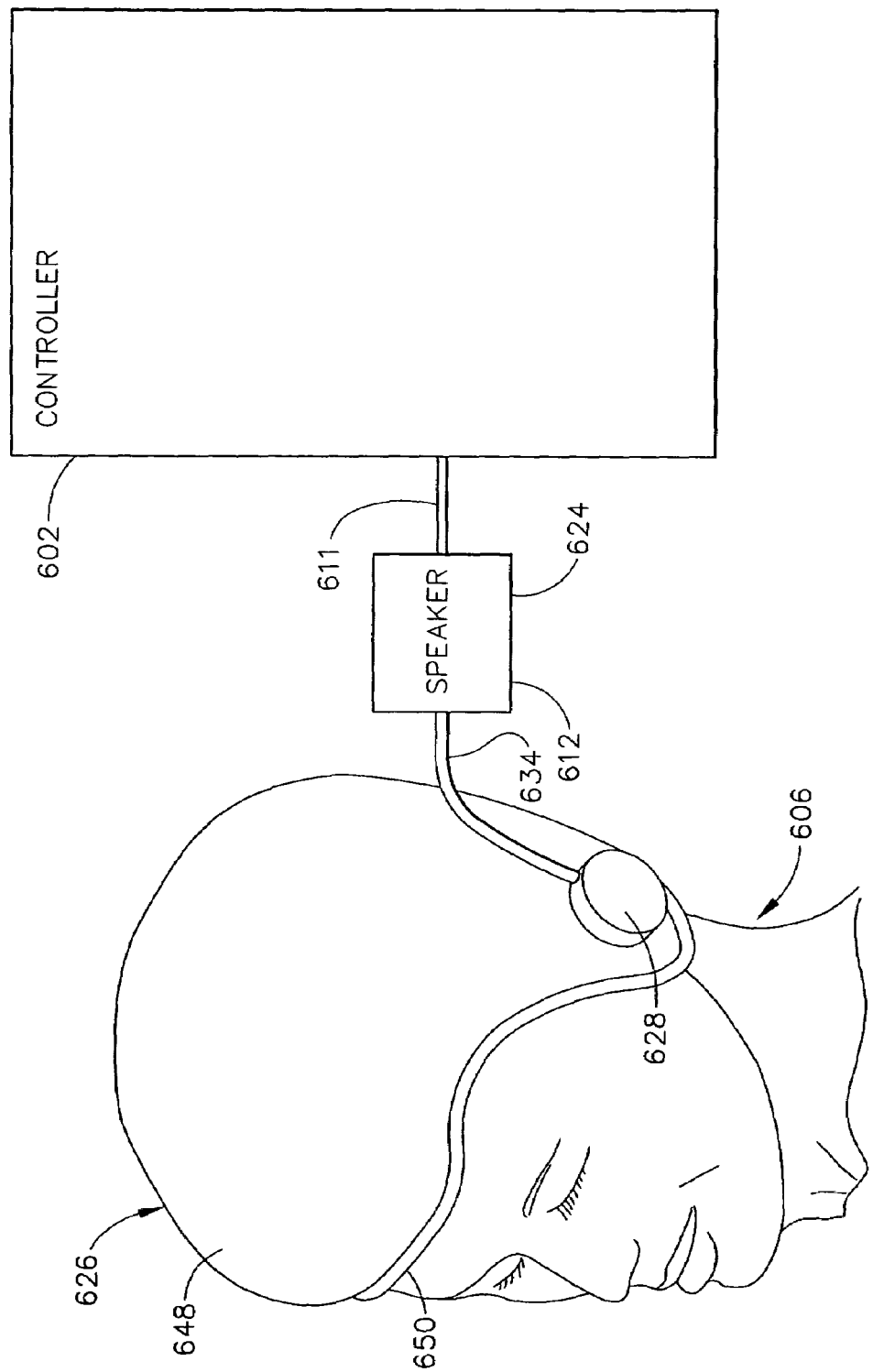
Figure 6:
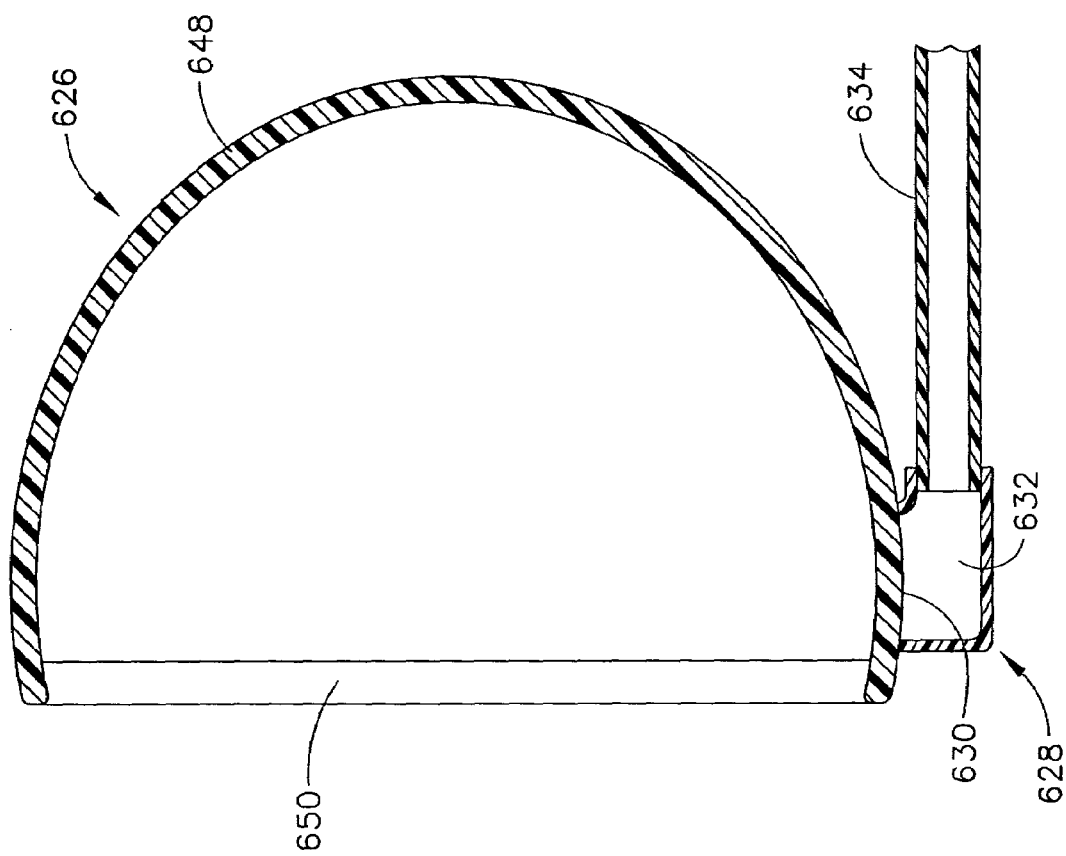

Advantages and benefits of one or more of the expressions of the embodiment and examples, etc. of FIGS. 5-1 to 5-6 include a finer determination of the level of sedation of a patient undergoing a medical procedure involving conscious sedation. In one application, the change in the determined levels of sedation over time (i.e., the rate of sedation) is computed and used to predict the level of sedation at a future time. The motor-biased handgrip example allows a handgrip to be adjusted to accommodate the different grip strengths of different patients. In those examples which eliminate external switches, such switch elimination provides for greater reliability as switches need to be sealed against moisture and debris.

Conscious Sedation Involving a Non-Ear-Canal-Contacting Speaker

A sixth aspect of the invention relates to conscious sedation and involves a non-ear-canal-contacting speaker. Referring now to the drawings, FIG. 6-1 illustrates a first embodiment of the sixth aspect of the invention. A first expression of the first embodiment is for a conscious sedation system 600 including a controller 602 and a response testing apparatus 604 (wherein parts 604a and 604b are parts of the response testing apparatus 604). The controller 602 generates a request for a predetermined response from a patient 606 and analyses at least a response made by the patient 606 to the request to determine a level of sedation of the patient 606. The response testing apparatus 604 includes a request assembly 608 and a response assembly 610. The request assembly 608 audibly communicates to the patient 606 the request generated by the controller 602 and includes a non-ear-canal-contacting speaker 612. The response assembly 610 senses the response and communicates the response to the controller 602.

In one construction, a cable 611 operatively connects the controller 602 to the request assembly 608 and a cable 613 operatively connects the response assembly 610 to the controller 602. In one variation, the response assembly 610 includes a handpiece (not shown) which senses a response of the patient to the request (such as sensing the patient pushing a button or moving the handpiece). In another variation, the response assembly 610 includes a sound detector (e.g., a microphone) which senses a vocal response made by the patient to the request (such as sensing the patient speaking). Other variations of the response assembly 610 are left to the artisan.

In one example of the speaker 612 of FIG. 6-1, the speaker 612 is a first speaker 614 as shown in FIG. 6-2. The first speaker 614, when disposed on the patient 606 proximate a bone of the patient 606, audibly communicates the request to the patient 606 at least in part by bone conduction of audible sound.

A first method of the invention, employing the first speaker 614, is for audibly communicating to a patient 606 a request generated by a controller 602 of a conscious sedation system 600 for a predetermined response from the patient 606, wherein the controller 602 analyzes at least a response made by the patient 606 to the request to determine a level of sedation of the patient 606. One step includes obtaining a first speaker 614. Another step includes disposing the first speaker 614 proximate a bone of the patient 606. An additional step includes audibly communicating to the patient 606 the request made by the controller 602 at least in part by bone conduction of audible sound using the first speaker 614.

In one employment of the first method, the first speaker 614 is disposed upon the skin or scalp of the patient 606 in the mastoid or skull area or elsewhere such as the neck or shoulder area. The first speaker 614, utilizing an acoustic transducer vibrator, provides vibration/sound in the audible frequency range. The sounds are perceived primarily by the patient 606 via bone conduction which bypasses the tympanic membrane of the ear and directly vibrates the cochlea of the ear for the patient 606 to hear the sounds.

In another example of the speaker 612 of FIG. 6-1, the speaker 612 is a second speaker 616 as shown in FIG. 6-3. In this example, the request assembly 608 also includes a pillow 618, wherein the second speaker 616 is disposed in the pillow 618. In one variation, an acoustic coupling gel 638 is disposed in the pillow 618. The cable 611 is also shown in FIG. 6-3.

A second method of the invention, employing the second speaker 616, is for audibly communicating to a patient 606 a request generated by a controller 602 of a conscious sedation system 600 for a predetermined response from the patient 606, wherein the controller 602 analyzes at least a response made by the patient 606 to the request to determine a level of sedation of the patient 606. One step includes obtaining a second speaker 616. Another step includes obtaining a pillow 618. An additional step includes disposing the second speaker 616 in the pillow 618. A further step is disposing the pillow 618 proximate the head of the patient 606. An added step includes audibly communicating to the patient 606 the request made by the controller 602 using the second speaker 616.

In an additional example of the speaker 612 of FIG. 6-1, the speaker 612 is a third speaker 620 as shown in FIG. 6-4. In this example, the request assembly 608 also includes a skull cap 622. The third speaker 620 is attached to the outside of the skull cap 622. When the skull cap 622 is worn on the head of the patient 606, the inside of the skull cap 622 covers an ear of the patient 606 and the third speaker 620 is substantially aligned with the ear canal of the patient 606.

A third method of the invention, employing the third speaker 620, is for audibly communicating to a patient 606 a request generated by a controller 602 of a conscious sedation system 600 for a predetermined response from the patient 606, wherein the controller 602 analyzes at least a response made by the patient to the request to determine a level of sedation of the patient 606. One step includes obtaining a third speaker 620. Another step includes obtaining a skull cap 622. An additional step includes attaching the third speaker 620 to the outside of the skull cap 622 so that, when the skull cap 622 is worn on the head of the patient 606, the inside of the skull cap 622 covers an ear of the patient 606 and the third speaker 620 is substantially aligned with the ear canal of the patient 606. A further step is disposing the skull cap 622 on the head of the patient 606. An added step includes audibly communicating to the patient 606 the request made by the controller 602 using the third speaker 620.

In a further example of the speaker 612 of FIG. 6-1, the speaker 612 is a fourth speaker 624 as shown in FIG. 6-5. In this example, the request assembly 608 also includes a skull cap 626 and a tube connector 628 attached to the outside of the skull cap 626 as shown in FIGS. 6-5 and 6-6. The tube connector 628 includes a sound-tube attachment site 630 and includes a sound passageway 632 extending from the outside of the skull cap 626 to the sound-tube attachment site 630. In one design, a sound tube 634 is operatively connected to the fourth speaker 624 and to the sound-tube attachment site 630. Other examples of a non-ear-canal-contacting speaker 612 are left to the artisan and include, without limitation, a hospital-bed-supported speaker and a floor-stand-supported speaker.

A fourth method of the invention, employing the fourth speaker 624, is for audibly communicating to a patient 606 a request generated by a controller 602 of a conscious sedation system 600 for a predetermined response from the patient 606, wherein the controller 602 analyzes at least a response made by the patient 606 to the request to determine a level of sedation of the patient 606. One step includes obtaining a fourth speaker 624. Another step includes obtaining a skull cap 626 and a tube connector 628 attached to the outside of the skull cap 626, wherein the tube connector 628 includes a sound-tube attachment site 630 and a sound passageway 632 extending from the outside of the skull cap 626 to the sound-tube attachment site 630, and wherein, when the skull cap 626 is worn on the head of the patient 606, the inside of the skull cap 626 covers an ear of the patient 606 and the sound passageway 632 at the outside of the skull cap 626 is substantially aligned with the ear canal of the patient 606. An additional step includes obtaining a sound tube 634. A further step includes operatively connecting the sound tube 634 to the fourth speaker 624 and to the sound-tube attachment site 630. Yet another step is disposing the skull cap 626 on the head of the patient 606. An added step includes audibly communicating to the patient 606 the request made by the controller 602 using the fourth speaker 624.

A second expression of the embodiment of FIG. 6-1 is for a request assembly 608 for a response testing apparatus 604 for a conscious sedation system 600, wherein the conscious sedation system 600 includes a controller 602 which generates a request for a predetermined response from a patient 606. The request assembly 608 includes a non-ear-canal-contacting speaker 612 which audibly communicates to the patient 606 the request generated by the controller 602.

In one example of the second expression of the embodiment of FIG. 6-1, the speaker 612 is a first speaker 614 as shown in FIG. 6-2. In this example, the first speaker 614, when disposed on the patient 606 proximate a bone of the patient 606, audibly communicates the request to the patient 606 at least in part by bone conduction of audible sound. In one implementation utilizing the first speaker 614, the request assembly 608 also includes a headband 636, the first speaker 614 is attached to the headband 636, and, when the headband 636 is worn by the patient 606, the first speaker 614 contacts a side of the head of the patient 606 above the ear. In another implementation, the first speaker 614 is attached to the patient using double-sided adhesive tape or an elastomeric band or a metallic band. In one construction, the first speaker 614 is devoid of any sound-emitting opening.

In another example of the second expression, the speaker 612 is a second speaker 616 as seen in FIG. 6-3. In this example, the request assembly 608 also includes a pillow 618, and the second speaker 616 is disposed in the pillow 618. In one variation, the request assembly 608 also includes an acoustic coupling gel 638 or an elastomeric pad disposed in the pillow 618. Examples of acoustic coupling gels 638 are left to the artisan. In one utilization, when the head of the patient 606 is disposed against the pillow 618, the sound path between the second speaker 616 and the ear of the patient 606 is substantially defined by the acoustic coupling gel 638. In one modification, the request assembly 608 also includes a single-use pillow cover (not shown) which covers the pillow 618 and which is exchanged with another single-use pillow cover before use by the next patient.

In an additional example of the second expression, the speaker 612 is a third speaker 620 as seen in FIG. 6-4. In this example, the request assembly 608 also includes a skull cap 622, the third speaker 620 is attached (either fixedly attached or removably attached such as with adhesive tape) to the outside of the skull cap 622, and, when the skull cap 622 is worn on the head of the patient 606, the inside of the skull cap 622 covers an ear of the patient 606 and the third speaker 620 is substantially aligned with the ear canal of the patient 606. In one implementation utilizing the third speaker 620, the request assembly 608 also includes a cable connector 640 (such as a socket or a plug) attached (either fixedly attached or removably attached such as with adhesive tape) to the outside of the skull cap 622 and includes a cord 642 operatively connecting (such as being hard wired to) the cable connector 640 and the third speaker 620. In another variation, not shown, the cord 642 is omitted and the cable connector 640 is attached directly to the third speaker 620. In one arrangement, the request assembly 608 also includes a cable 611, wherein the cable 611 is operatively connectable to the controller 602 (such as being hard wired to the controller 602) and to the cable connector 640 (such as being connectable to the cable connector 640 via a mating socket/plug 646). In one extension of the example of the third speaker 620, with or without contact of the third speaker 620 with the ear canal of the patient 606, the skull cap 622 has one or more sound holes (not shown) between the third speaker 620 and the ear canal of the patient 606.

In a further example of the second expression, the speaker 612 is a fourth speaker 624 as seen in FIGS. 6-5 and 6-6. In this example, the request assembly 608 also includes a skull cap 626 and a tube connector 628 attached (either fixedly attached or removably attached such as with adhesive tape) to the outside of the skull cap 626. In this example, the tube connector 628 includes a sound-tube attachment site 630 and includes a sound passageway 632 extending from the outside of the skull cap 626 to the sound-tube attachment site 630. In one implementation, when the skull cap 626 is worn on the head of the patient 606, the inside of the skull cap 626 covers an ear of the patient 606 and the sound passageway 632 at the outside of the skull cap 626 is substantially aligned with the ear canal of the patient 606. In one arrangement, the request assembly 608 also includes a sound tube 634, wherein the sound tube 634 is operatively connectable to the fourth speaker 624 and to the sound-tube attachment site 630. In one variation, the skull cap 626 has one or more sound holes (not shown) between the tube connector 628 and the ear canal of the patient 606. In another variation, the skull cap 626 is omitted and the end of the sound tube 634 distant the fourth speaker 624 is disposed proximate (including in) the ear canal of the patient.

In one construction involving the third and/or fourth speaker 620/624, the skull cap 622/626 includes a plastic film 648 having a periphery and an elastic band 650 attached to the plastic film 648 proximate the periphery as found in some shower caps. In an alternate construction, not shown, the skull cap 622/626 has a swimming-cap type of construction. Other constructions are left to the artisan. In one extension of the third and/or fourth speaker 620-624, with or without contact of the speaker with the ear canal, the third and/or fourth speaker 620/624 has a food-worker-hair-net type of construction.

A third expression of the embodiment of FIG. 6-1 is for a request assembly 608 for a response testing apparatus 604 for a conscious sedation system 600, wherein the conscious sedation system 600 includes a controller 602 which generates a request for a predetermined response from a patient 606. The request assembly 608 includes a non-ear-canal-contacting speaker 612/624 which audibly communicates to the patient 606 the request generated by the controller 602. The request assembly 608 also includes a sound tube 634 (as seen in FIG. 6-5) having one end disposable proximate an ear canal or a microphone of an assistive hearing device (such as a hearing aide) of the patient 606 and having another end disposable proximate the speaker 612/624. In one variation, the one end is disposable in the ear canal of the patient 606. In one arrangement, the speaker 612/624 is attachable to, or supportable by, the bed of the patient 606 or by an IV pole.

Any one or more of the previous embodiments, expressions, and methods can be extended, as appropriate, to provide sound to both ears of the patient, as can be appreciated by the artisan. In one variation, a switch or switches are provided to turn on and shut off providing sound to each ear of the patient.

Advantages and benefits of one or more of the expressions (but not necessarily extensions thereof) of the embodiments of FIGS. 6-1 to 6-6 include not having direct contact of the speaker with the ear canal of the patient 606. This design eliminates secretions of the ear canal of the patient from entering the speaker 612 which otherwise would have to be cleaned between patient use. Because no device enters the ear canal, this design provides more comfort for the patient and is compatible with patients with hearing aids. In the example employing the first speaker 614, no ear of the patient 606 is covered by any apparatus of the request assembly 608 adding to patient comfort and allowing the doctor to communicate with the patient, if desired, without having to remove a headset or an earphone from the ear or ears of the patient. In the example employing the second speaker 616, embedding a speaker in a pillow allows, in one arrangement, use of a replaceable (including a single-use) pillow cover. Any single-use device eliminates the need for cleaning between patient use. In the example employing the third speaker 620, having a skull cap 622 with attached third speaker 620 and cord connector 640 allows, in one arrangement, a single-use skull cap 622 employing an inexpensive or removably-attachable third speaker 620 (and optionally cord connector 640). In the example employing the fourth speaker 624, the use of a removably-attachable sound tube 634 to connect with the skull cap 626 allows, in one arrangement, a single-use skull cap 626 employing an inexpensive or removably-attachable tube connector 628. It is noted that a non-ear-canal-contacting speaker accommodates hearing-impaired patients by communicating with an assistive hearing device, such as a hearing aid, worn by such patients.

Conscious Sedation Involving Personalized Audio Requests

It is known in conscious sedation that when a patient is sedated and receives an audio stimulus request, the patient is more responsive to the audio request when there is a personalized message, the personalized message having a voice, word, phrase or sound with which the patient is familiar especially one which has a personal association or is emotionally evoking with the patient. Examples of personalized messages that the patient is more responsive to include a message addressing the patient by his name or a message using a voice that the patient is familiar with such as a family member or a doctor. Other examples of messages may be sounds that are attention-getting with a particular focus from the patient's perspective such as a dog bark or a siren.

Figures 1, 7:
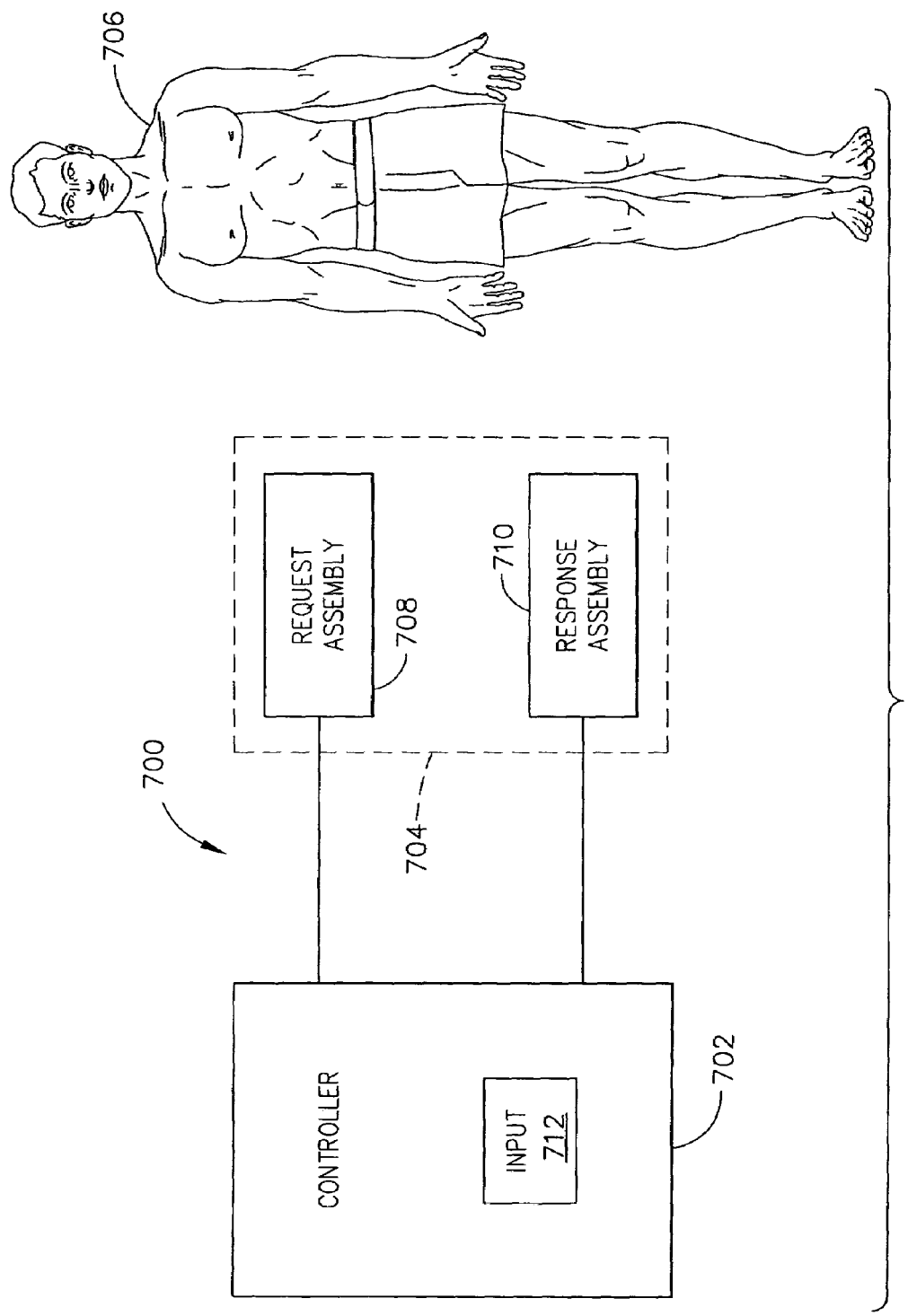

A seventh aspect of the invention relates a conscious sedation system which generates an audio request with a personalized message. FIG. 7-1 illustrates an embodiment of the seventh aspect of the invention. An embodiment of the invention is for a conscious sedation system 700 including a controller 702 and a response testing apparatus 704, wherein the controller 702 generates a request for a predetermined response generated by the patient 706 to the request, and wherein the controller includes an input 712 wherein a personalized message can be included in the request. The response testing apparatus 704 includes a request assembly 708 and a response assembly 710. The request assembly 708 communicates to the patient 706 the request generated by the controller 702, the request having a personalized message. The response assembly 710 is used by the patient 706 to generate the response and communicates the response to the controller 702.

In an embodiment of the invention, the input 712 can be a keypad or touch screen or other input device, wherein the patient's information is put into the controller. The keypad or touch screen may contain a text-to-speech software so that the patient's information can be converted to speech through voice synthesis and included in the personalized message. By addressing the sedated patient by name in the form of a personalized message, the patient is more likely to respond to the request. In addition to addressing the patient by name, the personalized message can also include a command such as "please squeeze your hand" or "please release your hand." The message can be used to instruct the patient on how to respond to various audible, tactile or other stimulation encountered during the procedure. Accordingly, the personalized message can be a supplement to or part of the request or it can be the request itself.

Another embodiment is an input that includes a microphone to enter the patient's information or a message to be included in the personalized message. The microphone further allows voices of specific persons to be recorded into the personalized message. For instance, a the patient's doctor or relative or a person to whom the patient is acquainted may record his own voice into a personalized message. In this way, the sedated patient is more likely to respond when he hears the familiar voice. In a preferred embodiment, the personalized message is recorded and saved as a wav file in the controller memory. The controller can then output the wav file or a combination of wav files as the personalized message. For instance, the controller may combine a wav file for "mister" or "misses" with a wav file containing the patient's name incorporating them into a personalized message. In another manifestation of the preferred embodiment, voice recognition software is used to convert the patient's name and information into text to be displayed on the screen for data entry, which may be manually corrected. The patient's name may be used later for playback as a request. The personalized message can also be manually or automatically revised during the procedure to reduce the tendency for the patient to adapt to the audio stimulus. The personalized message can be adapted automatically to change words in accordance with preset selections or in accordance with the patient's response; For example, the words which produce the greatest or most reliable patient response through the procedure may be used to assure a greater likelihood of getting a response as the patient becomes more deeply sedated. Other examples of personalized messages include those that have a directly relevant contextual tonal message, such as a voice speaking in a unique dialect or accent pattern particular to the patient; this provides for enhanced interest and comprehension versus a more generic version of the same language which leads to more effective audio stimulation. The personalized message may also be linguistically adapted for patients residing in specific localities of a region. Finally, the audio stimulus may also be a sound or song with which the patient is familiar.

In a further embodiment of the invention, the personalized message may be stored as memory in either the controller or the response testing assembly, wherein the memory is either digital or analog. The personalized message may be transferable from the controller to the response testing assembly by cable or wireless means and vice versa. In one manifestation of an embodiment of the invention, the message may be played in accordance with a predetermined time schedule. For example, it may be synchronized to occur in conjunction with the onset of each request or vibration period or it may utilize an adaptive audio stimulation timing in accordance with the patient's responsiveness such as not issuing the message unless successive vibrational attempts have failed to obtain a patient response. This reduces the tendency for the patient to habituate to the audio stimulation.

In yet a further embodiment of the invention, the input may be an auxiliary input signal connector for the user to input voice or sound data from an external source such as an external microphone or an external audio source. The audio source may be an analog audio source such as a tape recorder or a digital source such as CD, MP3 etc. Further, the system may include a CD or tape player for accepting input from a storage media that contains components of the personalized message.

In the example of the expression of the embodiment of FIG. 7-1, the controller 702 determines a delivery schedule of a conscious sedation drug to the patient 706 based at least in part on the determined level of sedation of the patient 706. The drug delivery apparatus has been omitted from FIG. 7-1 for clarity. A conscious sedation drug is a drug or drug combination which, in an efficacious amount, is capable of sedating the patient 706 during a medical procedure (such as a colonoscopy) while keeping the patient 706 conscious. Conscious sedation drugs, such as Propofol, are well known in the medical art. In one alternative, a doctor, instead of the controller 702, determines a delivery schedule of the conscious sedation drug to the patient 706 based at least in part on the determined level of sedation of the patient 706.

Conscious Sedation Using Finger Movement Response Assembly

Figures 1, 8:
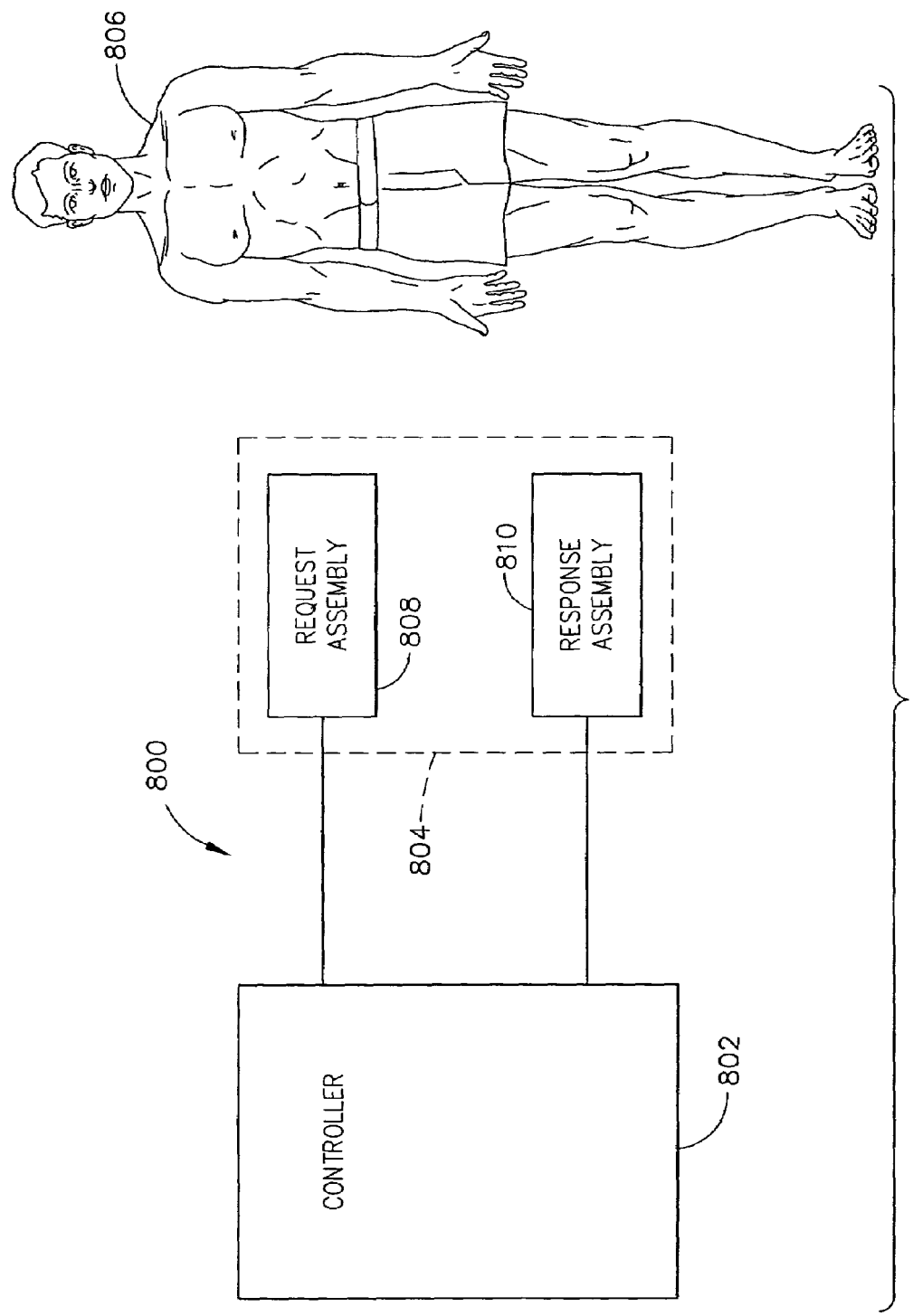
Figures 2, 8:
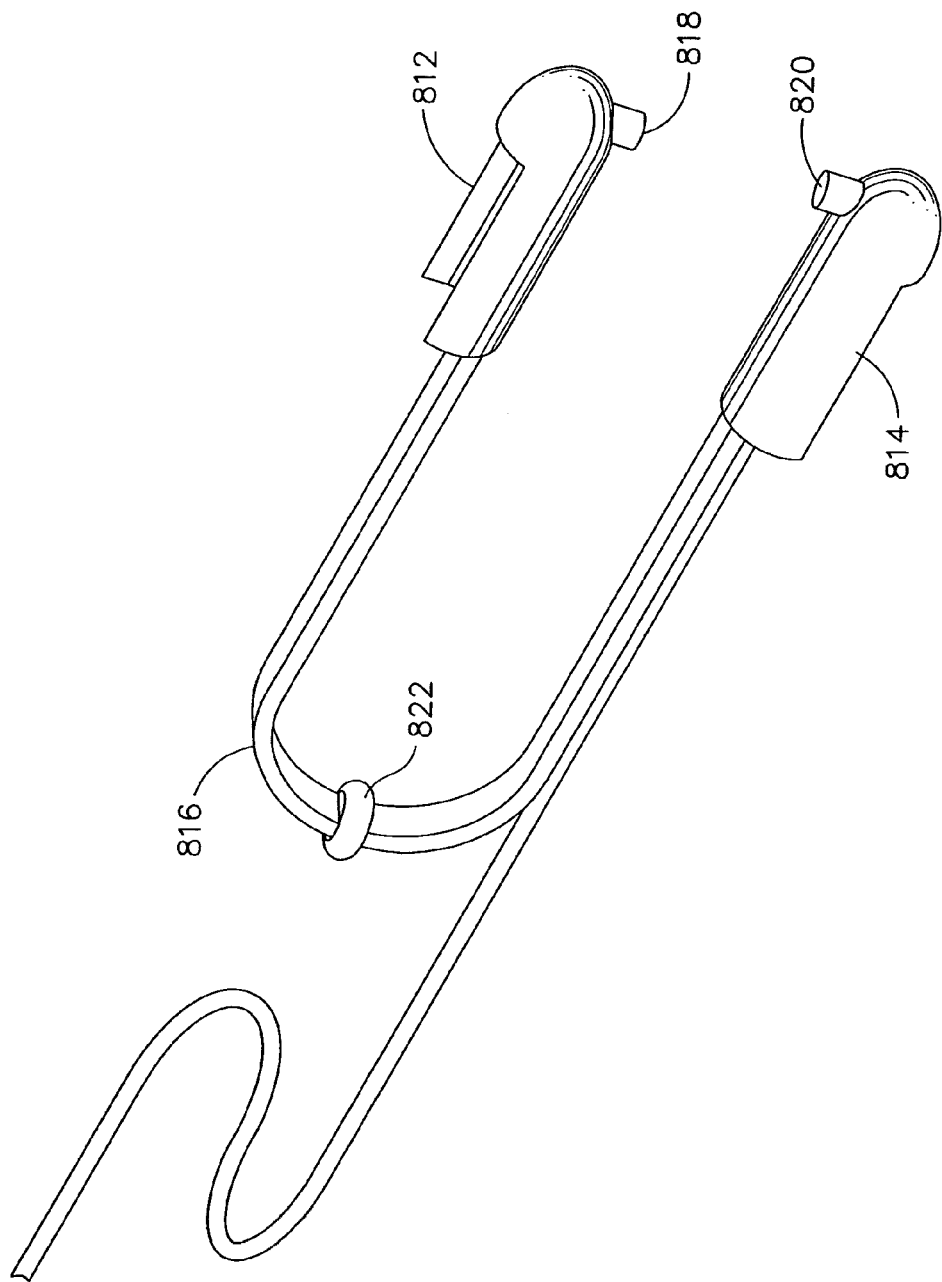
Figures 3, 8:
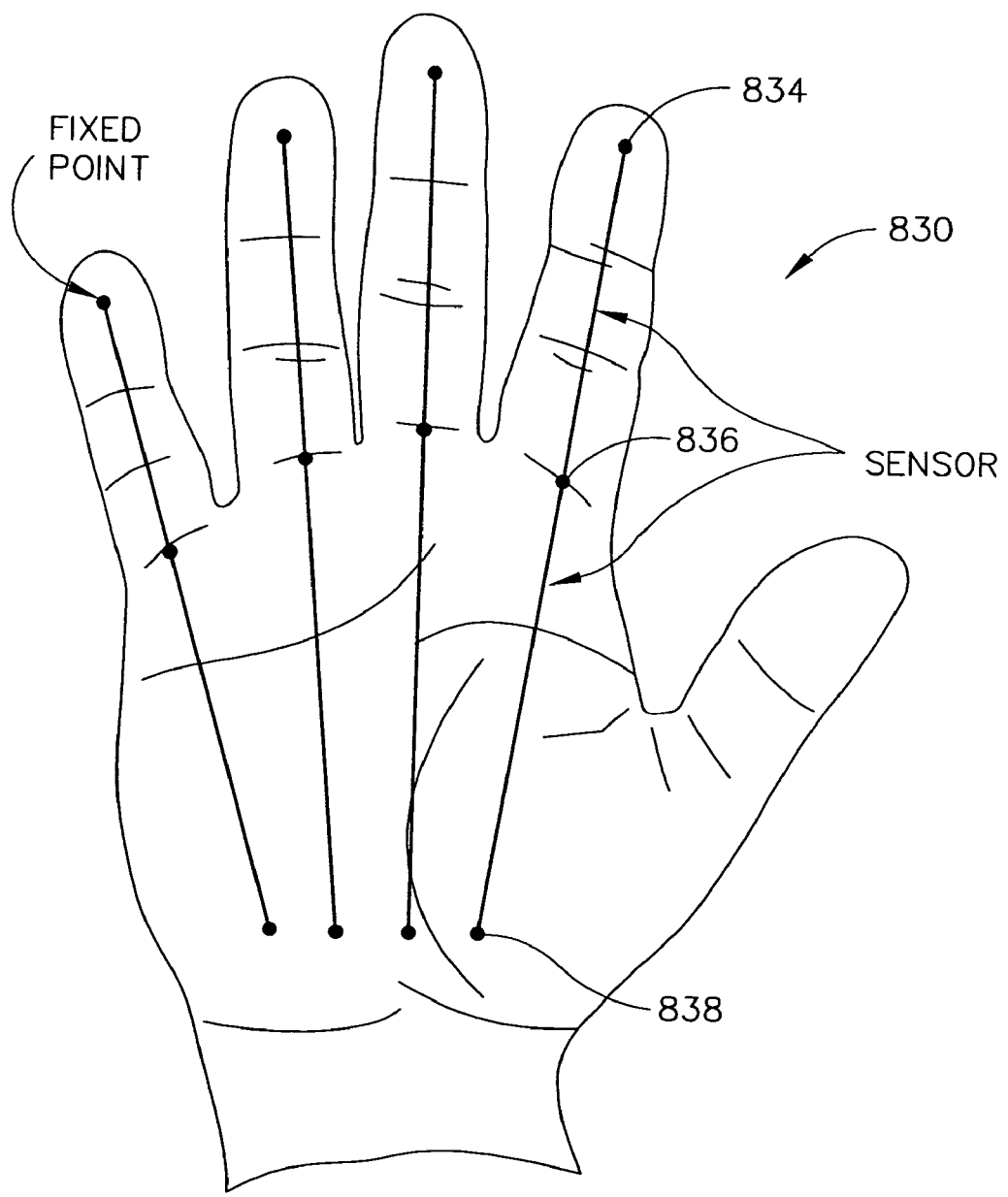

An eighth aspect of the invention relates to finger movement response testing for conscious sedation. FIG. 8-1 illustrates an embodiment of the eighth aspect of the invention. An embodiment of the invention is for a conscious sedation system 800 including a controller 802 and a response testing apparatus 804. The controller 802 generates a request for a predetermined response from a patient 806 to the request to determine a level of sedation of the patient 806 The response testing apparatus 804 includes a request assembly 808 and a response assembly 810. In a manifestation of the invention, either the response assembly 810 or the request assembly 808 is a finger attachable apparatus. The finger attachable apparatus can be a response assembly 810 wherein the response is generated by the movement of the patient's fingers or the finger attachable apparatus can be a request assembly 808 wherein the request is generated via the controller. In a further manifestation the finger attachable apparatus is both a response assembly and a request assembly in the response testing apparatus.

In one embodiment of the invention, the finger attachable apparatus is a finger touch response apparatus as shown in FIG. 8-2. The finger attachable apparatus comprises a first finger receptacle 812 and a second finger receptacle 814 that are attachable onto the patient's fingers. The receptacles 812, 814 are connected by a biasing member 816 that hold the receptacles 812, 814 apart. The biasing member 816 has a strain gage 822 located in the middle. At the ends of the receptacles 812, 814 are electrical contacts 818, 820. The finger touch response apparatus can be used as a response system, request system or both. As a request system, the finger receptacles 812, 814 can provide a stimulus to the patient's fingers. As a response system, the patient responds by trying to bring the receptacles 812, 814 in contact with each other by bringing the fingers together. The receptacles 812, 814 are connected by a biasing member 816 of a predetermined stiffness so that the receptacles do not inadvertently contact each other and can only contact each other when a sufficient force is applied by bringing the fingers together. At the end of the receptacles are electrical contacts 818, 820 that register a response when they are brought in contact with each other.

In a further embodiment of the invention, the biasing member 816 has a strain gage that measures the amount of force the patient is applying in attempting to contact or contacting the receptacles by bringing the fingers together.

Although the patient may not succeed in bringing the receptacles into contact, the amount of force the patient applies in his attempt can be measured. The higher the level of sedation of the patient, the less force he is able to generate in bringing the receptacles into contact with each other. Accordingly, the amount of force generated by the patient is correlated with the patient's level of sedation. Nevertheless, there is a minimum threshold force that the patient must apply in order for a response to be registered. Once that threshold force is exceeded, the strain gage continuously measures the amount of force that is applied. If the minimum threshold force is not met by the patient, there is no registered response.

In another embodiment of the invention, the finger attachable apparatus in FIG. 8-3 is a handpiece finger curl sensor mechanism 830 wherein the mechanism has fixed point sensors comprising finger sensors 834, knuckle sensors 836 and a palm stimulation source 838 to detect the curling movement of the patient's fingers towards the palm. The sensors are attached along the length of the fingers and the palm to detect the bending motion when the patient curls the fingers towards the palm. The handpiece finger curl sensor mechanism can be fitted onto the hand and comprises sensors that coincide with the fingers, knuckles and palm. The handpiece finger curl sensor mechanism 830 can be used as a response system, request system or both. As a request system, the palm stimulation source 838 can provide a stimulus to the patient's hand. As a response system, the patient responds by curling at least one or more fingers towards the palm or closing his hand over the palm stimulation source; a response can also be generated by uncurling the at least one or more finger away from the palm. In a further embodiment of the invention, the palm stimulation source is in the shape of a cylinder or sphere and is located in the palm of the hand wherein the patient generates a response by closing his hand over the palm stimulation source. The sensors measure the change in distance between the various locations on the hand. In yet a further embodiment of the invention, the handpiece is a glove that fits over the hand. The glove is stretchable so that the fingers are able to be curled towards the palm. The amount of stretch can also be measured by the sensors. The patient's ability to curl his fingers and/or close his hand diminishes as the patient becomes more sedated. Accordingly, the amount of finger curl or stretch by the patient correlates with the level of sedation of the patient.

The sensors of the finger curl sensor mechanism can be linear-displacement sensors (such as magnetometers or inductive sensors), a mercury-filled tube acting as a strain gage, or even electrodes monitoring changes in surface impedance. However, it should be noted that the sensors are not limited to the ones mentioned. The handpiece finger curl sensor mechanism also can be a glove such as a latex-free Nitrile glove. The response can also be selected from a series of sensors or from a collective response from various sensors.

In one example of the expression of the embodiment of FIG. 8-1, the controller 802 determines a delivery schedule of a conscious sedation drug to the patient 806 based at least in part on the determined level of sedation of the patient 806. The drug delivery apparatus has been omitted from FIG. 8-1 for clarity. A conscious sedation drug is a drug or drug combination which, in an efficacious amount, is capable of sedating the patient 806 during a medical procedure (such as a colonoscopy) while keeping the patient 806 conscious. Conscious sedation drugs, such as Propofol, are well known in the medical art. In one alternative, a doctor, instead of the controller 802, determines a delivery schedule of the conscious sedation drug to the patient 806 based at least in part on the determined level of sedation of the patient 806.

Conscious Sedation Involving Automated Audio Calibration

It is known that when a patient is sedated, his ability to discern audio stimulus is reduced. Therefore, in a conscious sedation system, the patient's ability to discern various levels of audio stimulus correlates with the patient's level of sedation. The higher the level of audio stimulus required for the patient to discern and generate a response, the more sedated the patient. However, because each patient has different initial levels of hearing, a baseline level of hearing needs to be established in order to use audio stimulus in assessing the patient's level of sedation. For example, one non-sedated patient may be able to discern a low level audio stimulus while another non-sedated patient may need a higher level of audio stimulus in order to discern or hear the stimulus. Accordingly, a baseline level of hearing needs to be established with each individual patient before using audio stimulus in a conscious sedation system to determine the patient's level of sedation by monitoring the patient's response to the audio stimulus.

In the prior art, the patient's baseline, namely the minimum threshold audio stimulus level at which the patient is able to hear the audio request in order to generate a response, is established manually. The doctor manually increases the intensity of the audio stimulus until the patient hears the stimulus and generates a request. The level of intensity at which the patient discerns the audio request is the baseline that will be used to in the conscious sedation system. Once this baseline is calibrated, it is used in the conscious sedation system to assess the level of sedation of the patient.

Figures 1, 9:
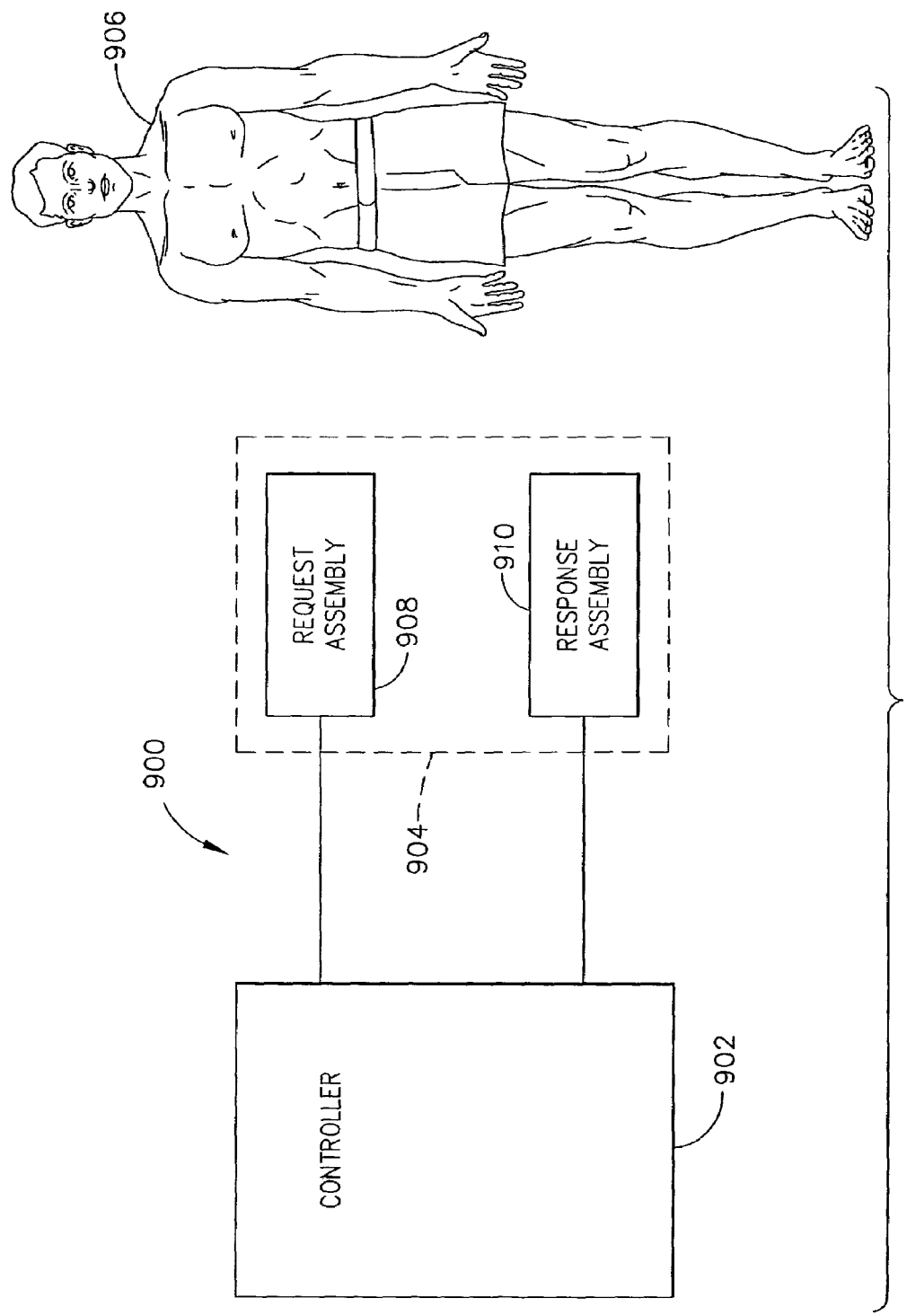
Figures 2, 9:
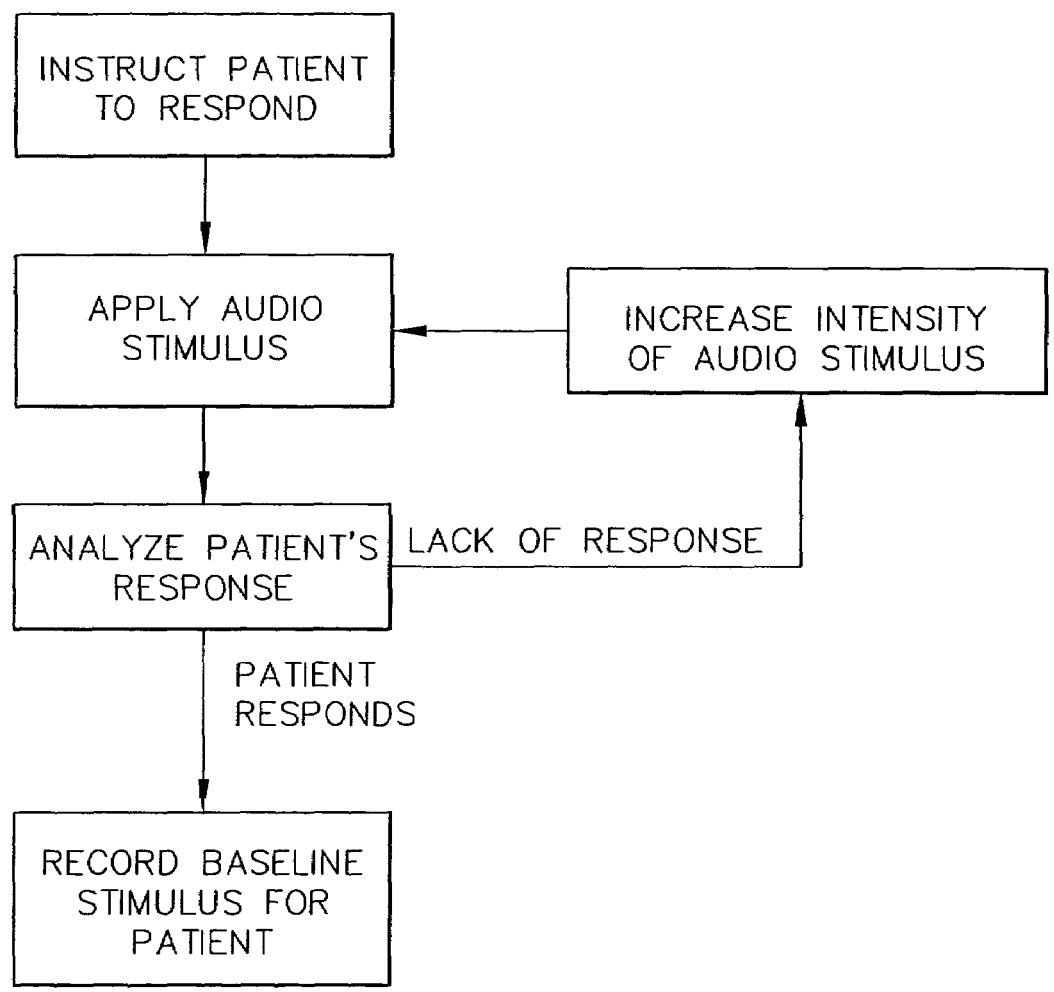
Figures 3, 9:
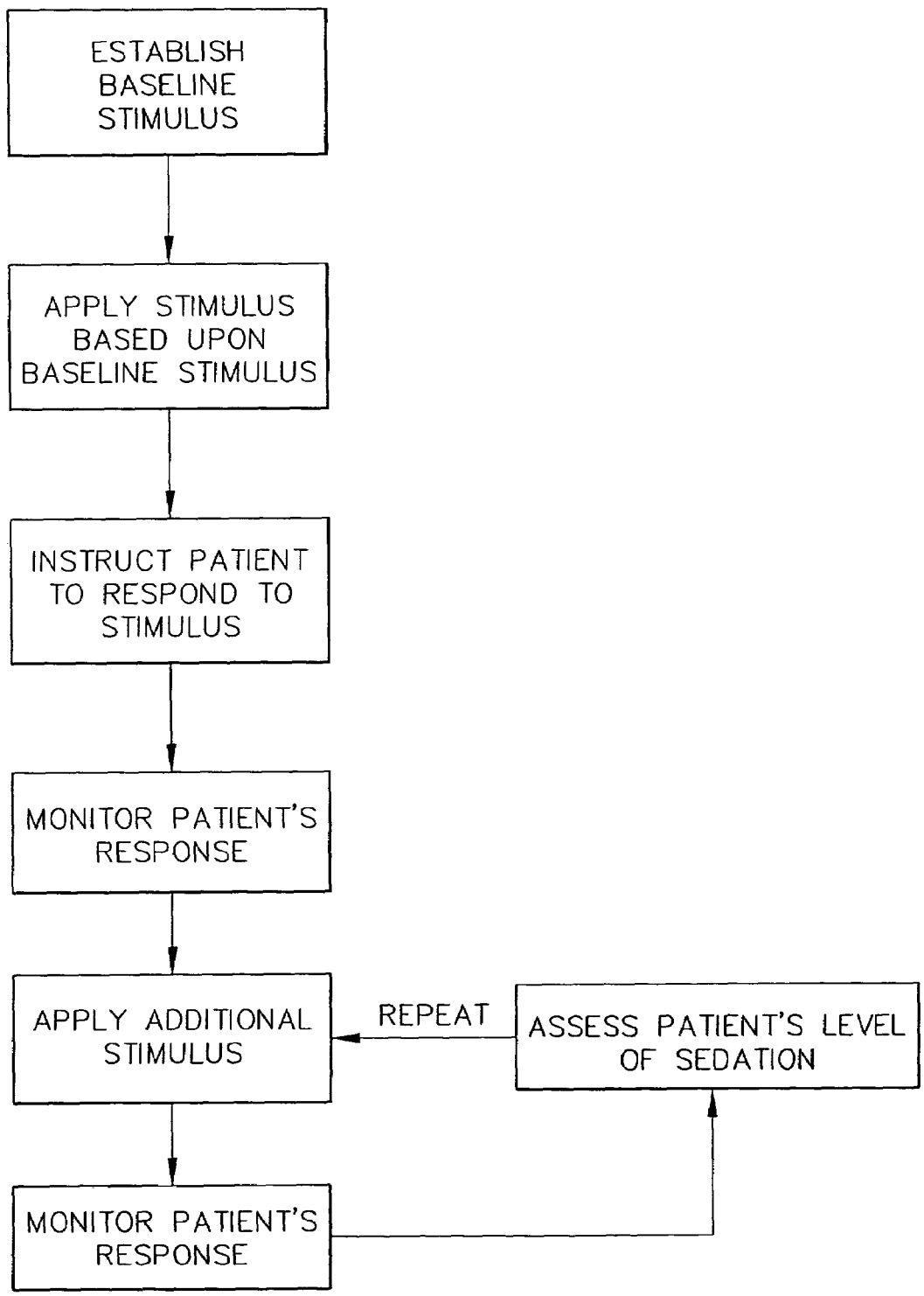
Figures 4, 9:
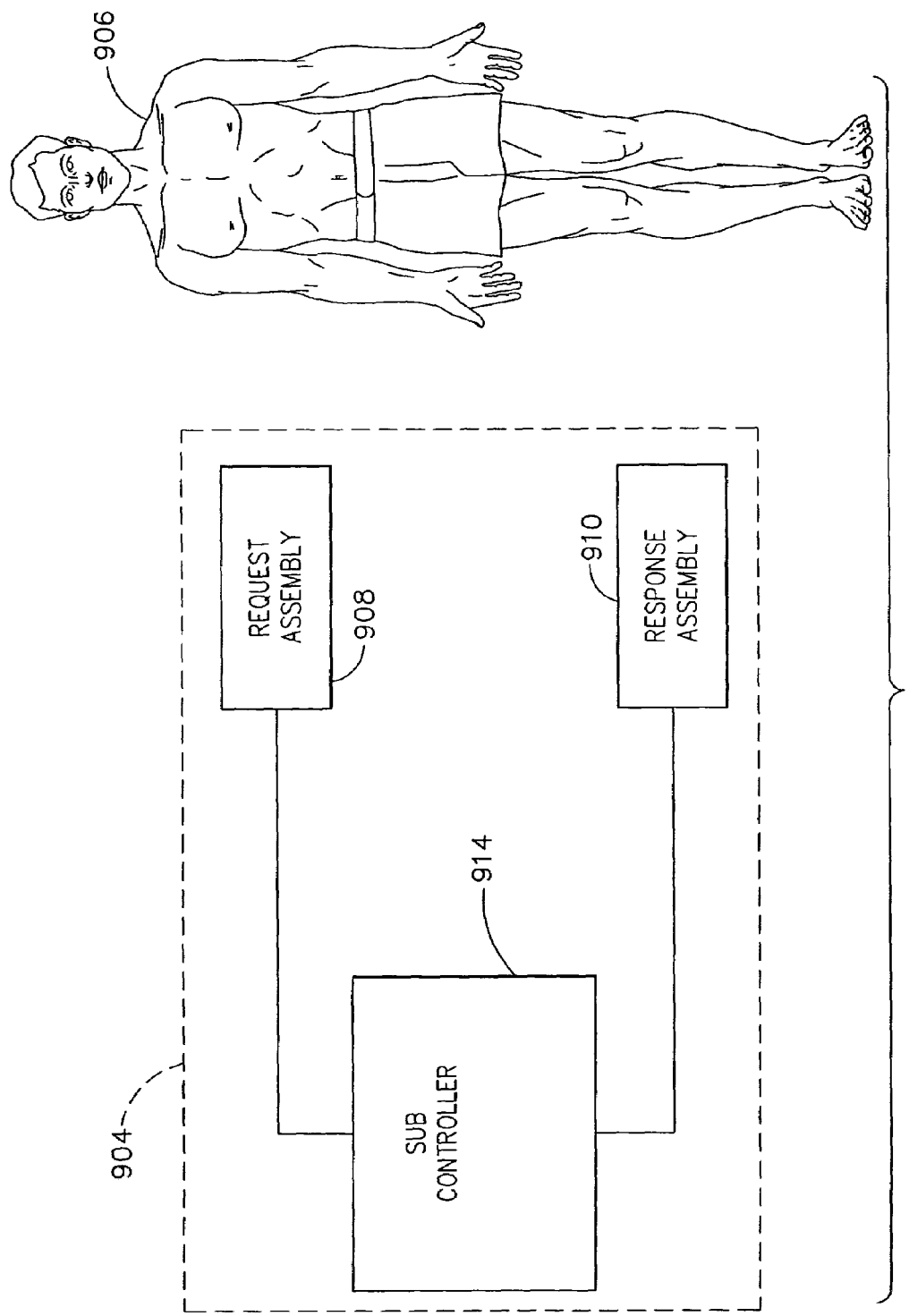

A ninth aspect of the invention relates to an audio calibration setting for a conscious sedation system. FIG. 9-1 illustrates an embodiment of the ninth aspect of the invention. An embodiment of the invention is for a conscious sedation system 900 including a controller 902 and a response testing apparatus 904, wherein the controller 902 is programmed to generate a request for a predetermined response from a patient 906 to the request, and wherein the controller 902 analyzes the response or lack thereof generated by the patient in order to calibrate the patient's level of hearing based on the patient's response to the request to establish a baseline audio stimulus and further to determine a level of sedation of the patient 906. The response testing apparatus 904 includes a request assembly 908 and a response assembly 910. The request generated can be a discrete or continuous audio stimulus.

Referring to FIG. 9-2, in another embodiment of the invention, a method for the automated audio calibration of a patient in a conscious sedation system is disclosed wherein the controller 902 generates a request to the patient, the request being an audio stimulus of very low amplitude. The controller 902 monitors the patient's predetermined response to the request. If the patient does not respond to the request because the amplitude of the stimuli is too low for the patient to perceive, another request is generated to the patient, the request being a slightly higher amplitude than the previous request. The process is repeated until the patient generates a predetermined response to the request. Once the response is generated, the controller records the level of stimulus at which the patient responded and calibrates the patient's baseline level of hearing based on the level of stimulus to which the patient responded. Once the patient's baseline level of hearing is established and recorded by the controller, the baseline is used as the initial stimulus level in assessing the level of sedation of the patient.

In a further embodiment of the invention as shown in FIG. 9-3, a method for the automated audio calibration of a patient's level of hearing and further determining the patient's level of sedation is taught. Once the baseline stimulus is established, an audio stimulus is generated to the patient based on the baseline stimulus by applying a first audio stimulus to the patient who has received, is receiving or is about to receive a conscious sedation drug. The patient is then instructed to respond to the audio stimulus. The patient's response to the audio stimulus is monitored and an additional audio stimulus is applied to the patient when the patient has received, is receiving or is about to receive a dose of a conscious sedation drug. The additional audio stimulus can be the same or different as the first audio stimulus. The patient's response to the additional audio stimulus is monitored again and the patient's level of sedation is assessed based on the patient's response. The steps of applying additional audio stimulus and monitoring the patient's response can be repeated to determine the patient's level of sedation.

Another expression of the embodiment of the invention is for a response testing apparatus 904 for a conscious sedation system. Referring to FIG. 9-4, the response testing apparatus 904 includes a request assembly 908, a response assembly 910, and a sub-controller 914 wherein the sub-controller 914 calibrates the patient's level of hearing based on the patient's response to establish a baseline level of hearing. The sub-controller 914 analyzes the response or lack thereof generated by the patient 906 in order to calibrate the patient's level of hearing based on the patient's response or lack thereof to the request to establish a baseline and further to determine a level of sedation of the patient 906. The sub-controller 914 monitors the patient's predetermined response to the request. If the patient does not respond to the request because the amplitude of the stimulus is too low for the patient to perceive, another request is generated to the patient, the request being a slightly higher amplitude than the previous request. The process is repeated until the patient generates a predetermined response to the request. Once the response is generated, the sub-controller 914 records the level of stimulus at which the patient responded and calibrates the patient's baseline level of hearing based on the level of stimulus to which the patient responded. Once the patient's baseline level of hearing is established and recorded by the sub-controller, the baseline is used as the initial stimulus level in assessing the level of sedation of the patient.

In one example of the embodiment of FIG. 9-1, the controller 902 determines a delivery schedule of a conscious sedation drug to the patient 906 based at least in part on the determined level of sedation of the patient 906. The drug delivery apparatus has been omitted from FIG. 9-1 for clarity. A conscious sedation drug is a drug or drug combination which, in an efficacious amount, is capable of sedating the patient 906 during a medical procedure (such as a colonoscopy) while keeping the patient 906 conscious. Conscious sedation drugs, such as Propofol, are well known in the medical art. In one alternative, a doctor, instead of the controller 902, determines a delivery schedule of the conscious sedation drug to the patient 906 based at least in part on the determined level of sedation of the patient 906.

It is understood that any one or more of the previously-described aspects, embodiments, expressions of embodiments, examples, methods, etc. can be combined with any one or more of the other previously-described aspects, embodiments, expressions of embodiments, examples, methods, etc. For example, and without limitation, cableless communication can be used in combination with personalized audio requests, etc.

The foregoing description of several aspects of the invention has been presented for purposes of illustration. It is not intended to be exhaustive or to limit the invention to the precise forms and procedures disclosed, and obviously many modifications and variations are possible in light of the above teaching. For example, as would be apparent to those skilled in the art, the disclosures herein of the conscious sedation systems, components thereof and methods therefor have equal application in robotic assisted surgery taking into account the obvious modifications of such systems, components and methods to be compatible with such a robotic system.

What is claimed is:

1. A conscious sedation system comprising:
 a) a controller which generates a request for a baseline response and a predetermined response from a patient and which analyses at least a response made by the patient to the request to determine a level of sedation of the patient; and
 b) a cannula which is disposable on the face of the patient proximate at least one of the nose and the mouth of the patient for monitoring the breathing of the patient; and
 c) a response testing apparatus including:
   (1) a request assembly which communicates to the patient the request generated by the controller; and
   (2) a response assembly which senses the response and which communicates the response to the controller, wherein the response testing apparatus is supported by the cannula.

2. The conscious sedation system of claim 1, wherein a user and/or the controller determines a delivery schedule of a conscious-sedation drug to the patient based at least in part on the determined level of sedation of the patient.

3. The conscious sedation system of claim 1, wherein the request assembly includes a first vibrator supported by the cannula.

4. The conscious sedation system of claim 3, wherein the first vibrator produces a tactile request to the face of the patient.

5. The conscious sedation system of claim 4, wherein the first vibrator is disposed in the cannula.

6. The conscious sedation system of claim 4, wherein the first vibrator is disposed on the cannula.

7. The conscious sedation system of claim 3, wherein the request assembly includes a second vibrator disposable to produce a tactile request to a site on the patient other than to the face of the patient.

8. The conscious sedation system of claim 7, wherein the controller at least compares responses of the patient to tactile requests from the first and second vibrators in determining the level of sedation of the patient.

9. The conscious sedation system of claim 5, wherein the first vibrator is the only vibrator of the request assembly producing a tactile request.

10. The conscious sedation system of claim 1, wherein the predetermined response is a patient head-generated response, and wherein at least a part of the response assembly is supported by the cannula.

11. The conscious sedation system of claim 10, wherein the patient head-generated response is a patient-generated vocal response, and wherein the response assembly includes a sound detector supported by the cannula.

12. The conscious sedation system of claim 11, wherein the controller at least uses at least one of the intensity and the tonal qualities of the vocal response in determining the level of sedation of the patient.

13. The conscious sedation system of claim 10, wherein the patient head-generated response is a patient-generated head movement response, and wherein the response assembly includes a motion sensor supported by the cannula.

14. The conscious sedation system of claim 10, wherein the patient head-generated response is a patient-generated breathing response, and wherein the response assembly includes a breathing sensor and/or a breathing-detection tube supported by the cannula.

15. The conscious sedation system of claim 14, wherein the patient-generated breathing response includes at least one of a yawn and a breath deeper than an immediate previous breath.

16. The conscious sedation system of claim 14, wherein the breathing sensor detects the pressure of the exhaled breathing of the patient.

17. A conscious sedation system comprising:
   a) a controller which generates a request for a baseline breathing response and a predetermined breathing response from a patient and which analyses at least a breathing response made by the patient to the request to determine a level of sedation of the patient; and
   b) a response testing apparatus including:
      (1) a request assembly which communicates to the patient the request generated by the controller; and
      (2) a cannula which is disposable on the face of the patient proximate at least one of the nose and the mouth of the patient for monitoring the breathing of the patient, wherein the cannula is operatively connected to the controller.

18. The conscious sedation system of claim 17 wherein a user and/or the controller determines a delivery schedule of a conscious-sedation drug to the patient based at least in part on the determined level of sedation of the patient.

19. A cannula and response testing assembly for a conscious sedation system comprising:
   a) a cannula which is disposable on the face of a patient proximate at least one of the nose and the mouth of the patient for monitoring the breathing of the patient; and
   b) a response testing apparatus including:
      (1) a request assembly which communicates to the patient a request generated by a controller of the conscious sedation system for a baseline response and a predetermined response from the patient; and
      (2) a response assembly which senses a response made by the patient to the request and which communicates the response to the controller which analyses at least the response to determine a level of sedation of the patient,
   wherein at least a part of at least one of the request and response assemblies is supported by the cannula.

20. The cannula and response testing assemblage of claim 19, wherein the request assembly includes a first vibrator supported by the cannula.

21. The cannula and response testing assemblage of claim 19, wherein the response is a patient head-generated response, and wherein at least a part of the response assembly is supported by the cannula.

22. The cannula and response testing assemblage of claim 21, wherein the response assembly includes at least one of a sound detector, a motion sensor, a breathing sensor, and a breathing-detection tube supported by the cannula.

* * * * *